(12) United States Patent
Skrabal

(10) Patent No.: US 10,517,499 B2
(45) Date of Patent: Dec. 31, 2019

(54) ECG DEVICE

(71) Applicant: Falko Skrabal, Graz (AT)

(72) Inventor: Falko Skrabal, Graz (AT)

(*) Notice: Subject to any disclaimer, the term of this patent is extended or adjusted under 35 U.S.C. 154(b) by 654 days.

(21) Appl. No.: 14/769,560

(22) PCT Filed: Feb. 21, 2014

(86) PCT No.: PCT/EP2014/053384
§ 371 (c)(1),
(2) Date: Aug. 21, 2015

(87) PCT Pub. No.: WO2014/128237
PCT Pub. Date: Aug. 28, 2014

(65) Prior Publication Data
US 2015/0374256 A1 Dec. 31, 2015

(30) Foreign Application Priority Data
Feb. 22, 2013 (AT) .................................. A 135/2013

(51) Int. Cl.
*A61B 5/0402* (2006.01)
*A61B 5/0408* (2006.01)
(Continued)

(52) U.S. Cl.
CPC ........ *A61B 5/04082* (2013.01); *A61B 5/0408* (2013.01); *A61B 5/04012* (2013.01);
(Continued)

(58) Field of Classification Search
USPC ................................................ 600/508–509
See application file for complete search history.

(56) References Cited

U.S. PATENT DOCUMENTS 4,628,939 A 12/1986 Little et al.
4,646,747 A 3/1987 Lundback
(Continued)

FOREIGN PATENT DOCUMENTS

AT         502921       6/2007
DE     102 49 863       5/2004
(Continued)

OTHER PUBLICATIONS

International Search Report for application No. PCT/EP2014/053384 dated Mar. 27, 2014.
(Continued)

*Primary Examiner* — Nicole F Lavert
*Assistant Examiner* — Nicole F. Johnson
(74) *Attorney, Agent, or Firm* — Workman Nydegger

(57) ABSTRACT

An ECG device comprising limb leads and chest wall leads is described which is also suitable for deriving the hemodynamic activity of the heart and the function of the vessels and, respectively, also for evaluating the fluid equilibrium. This is achieved in that at least part of the electrodes of the multichannel ECG is developed with additional embodiments for physical emissions and measurements, for example, electric current and voltage, pressure, sound vibrations, light, and that an electrode is provided for the current supply and, respectively, the voltage measurement at the upper thorax aperture. Furthermore, an alternating current field is built up between the electrodes or, respectively, the distance between the electrodes is used as an ion conductor. Thus, during the conventional ECG writing, the acceleration of the blood and hence the cardiac output, the valve closure and the valve opening, as well as the mechanics of individual circulation sections, for example, also the pulse wave transit time, the blood flow in body sections, the body
(Continued)

composition etc. can also be registered and output simultaneously with the routine ECG.

25 Claims, 7 Drawing Sheets

(51) Int. Cl.
*A61B 5/053* (2006.01)
*A61B 5/04* (2006.01)
*A61B 5/00* (2006.01)
*A61B 5/01* (2006.01)
*A61B 5/02* (2006.01)
*A61B 5/022* (2006.01)
*A61B 5/024* (2006.01)
*A61B 5/0285* (2006.01)
*A61B 5/0295* (2006.01)
*A61B 5/0452* (2006.01)
*A61B 5/11* (2006.01)

(52) U.S. Cl.
CPC .......... *A61B 5/0535* (2013.01); *A61B 5/0537* (2013.01); *A61B 5/4878* (2013.01); *A61B 5/721* (2013.01); *A61B 5/01* (2013.01); *A61B 5/02028* (2013.01); *A61B 5/0285* (2013.01); *A61B 5/0295* (2013.01); *A61B 5/02233* (2013.01); *A61B 5/02416* (2013.01); *A61B 5/04085* (2013.01); *A61B 5/04525* (2013.01); *A61B 5/1102* (2013.01); *A61B 5/6823* (2013.01); *A61B 5/6824* (2013.01); *A61B 5/6828* (2013.01); *A61B 5/6829* (2013.01); *A61B 5/6831* (2013.01); *A61B 5/6833* (2013.01); *A61B 5/6834* (2013.01); *A61B 5/6838* (2013.01); *A61B 2562/0219* (2013.01)

(56) References Cited

U.S. PATENT DOCUMENTS

| | | | |
|---|---|---|---|
| 4,807,638 A | 2/1989 | Sramek | |
| 6,339,722 B1 | 1/2002 | Heethaar et al. | |
| 6,560,481 B1 | 5/2003 | Heethaar et al. | |
| 7,110,804 B2 | 9/2006 | Baumer et al. | |
| 7,904,141 B2 | 3/2011 | Osypka et al. | |
| D675,738 S | 2/2013 | Baumer et al. | |
| 8,521,264 B2 | 8/2013 | Harrold et al. | |
| 2001/0030077 A1 | 10/2001 | Watson | |
| 2003/0163058 A1* | 8/2003 | Osypka | A61B 5/02007 600/513 |
| 2005/0033190 A1 | 2/2005 | Bauer | |
| 2005/0273015 A1 | 12/2005 | Bauer et al. | |
| 2008/0009757 A1 | 1/2008 | Tsoglin et al. | |
| 2008/0269625 A1* | 10/2008 | Halperin | A61B 5/113 600/508 |
| 2009/0227886 A1 | 9/2009 | Bauer et al. | |
| 2010/0324404 A1 | 12/2010 | Harrold et al. | |
| 2011/0257554 A1* | 10/2011 | Banet | A61B 5/0809 600/536 |
| 2011/0257555 A1* | 10/2011 | Banet | A61B 5/0809 600/538 |
| 2011/0319781 A1* | 12/2011 | Riemenschnider | A61B 5/04011 600/523 |
| 2012/0059593 A1 | 3/2012 | Konings | |
| 2013/0096448 A1 | 4/2013 | Brooks et al. | |

FOREIGN PATENT DOCUMENTS

| | | |
|---|---|---|
| DE | 10 2009 035 018 | 2/2009 |
| DE | 20 2008 014 621 | 4/2009 |
| EP | 1275342 | 1/2003 |
| EP | 2319411 | 5/2011 |
| FR | 2971137 | 8/2012 |
| WO | 89/03656 | 5/1989 |
| WO | 2004/030535 | 4/2004 |
| WO | 2006/020764 | 2/2006 |
| WO | 2006/063255 | 6/2006 |
| WO | 2008/031030 | 3/2008 |
| WO | 2009/033625 | 3/2009 |
| WO | 2012/092303 | 7/2012 |

OTHER PUBLICATIONS

Chaitman, et al. "Improved Efficiency of Treadmill Exercise Testing Using a Multiple Lead ECG System and Basic Hemodynamic Exercise Response" *Circulation*. 57:71-79. 1978.

Bertrand C.A., et al. "A Study of Heart Sounds and Murmurs by Direct Heart Recordings" *Circulation*. 8:49-57. 1956

Schuhfried, et al. "Fourier Analysis of Impedance Rheography for Peripheral Arterial Occlusive Disease" *European Journal of Applied Physiology* 89:384-86. 2003

Watt, et al. "Arterial Pressure Contour Analysis for Estimating Human Vascular Properties" *Journal of Applied Physiology* 40: 171-176. 1976.

"Spectral Analysis of Electrical Impedance Measurements on the Lower Limbs" IEEE Trans Biomed Eng 30: 387-91. 1983.

Zhu F., et al. "Segment-specific Resistivity Improves Body Fluid Volume Estimates From Bioimpedance Spectroscopy in Hemodialysis Patients" *Journal of Applied Physiology* 100:717-24. 2005.

Skrabal, F., et al.; *The Combyn™ ECG: Adding haemodynamic and fluid leads for the ECG. Part II: Prediction of total body water (TBW), extracellular fluid (ECF), ECF overload, fat mass (FM) and "dry" appendicular muscle mass (AppMM)*. Med Eng Phys. Jun. 2017;44:44-52. doi: 10.1016/j.medengphy.2017.03.002. Epub Mar. 31, 2017.

Skrabal, F., et al.; *Adding "hemodynamic and fluid leads" to the ECG. Part I: the electrical estimation of BNP, chronic heart failure (CHF) and extracellular fluid (ECF) accumulation*. Med Eng Phys. Jul. 2014;36(7):896-904; discussion 896. doi: 10.1016/j.medengphy. 2014.03.015. Epub May 1, 2014.

* cited by examiner

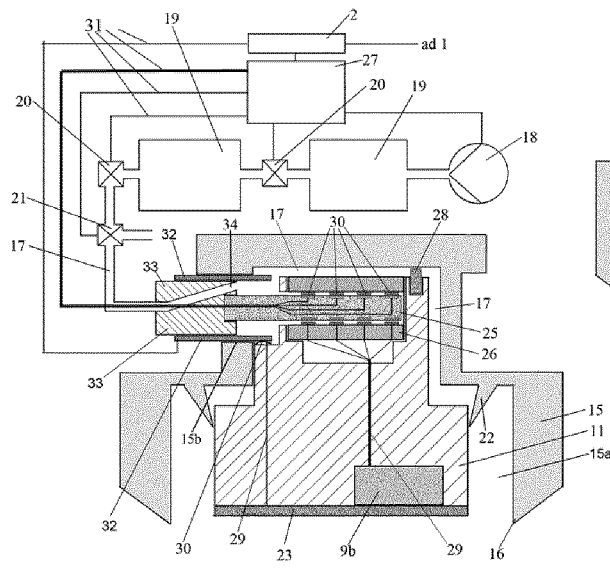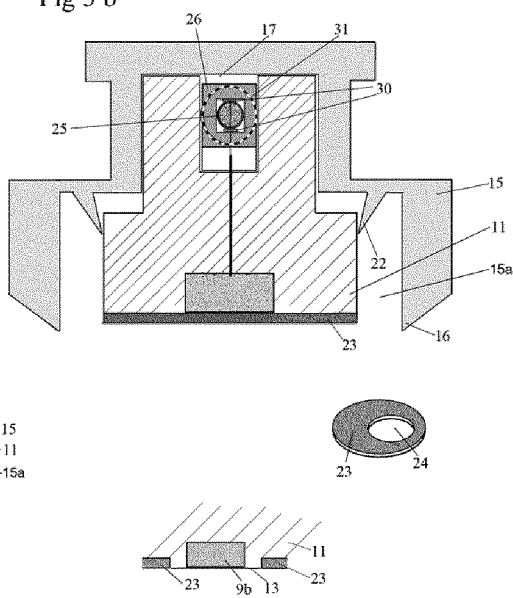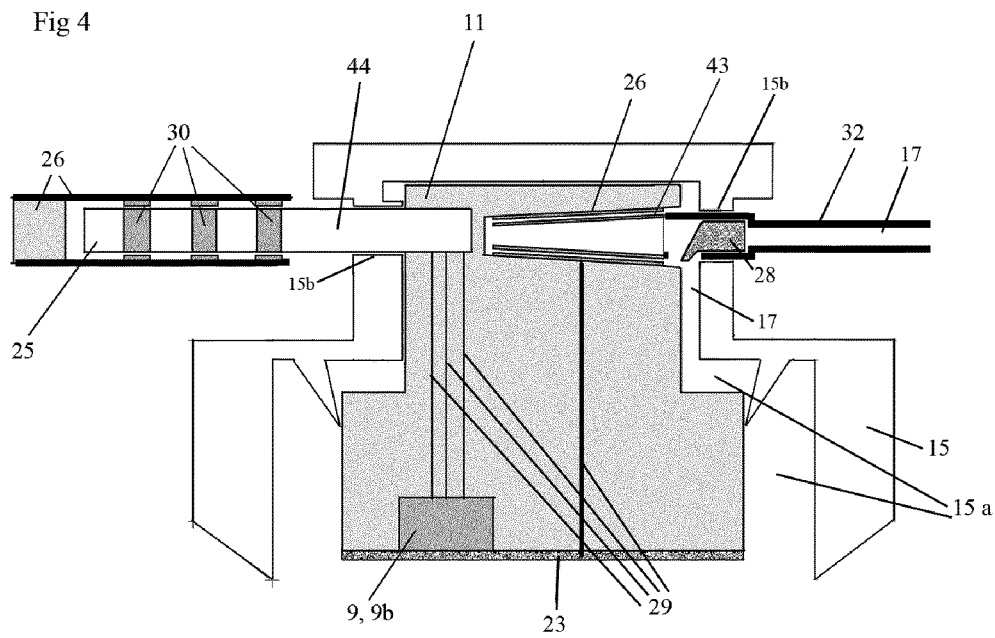

ECG DEVICE

CROSS REFERENCE TO RELATED APPLICATIONS

This application is a U.S. Nationalization of PCT Application Number PCT/EP2014/053384, filed on Feb. 21, 2014, which claims priority to Austrian Patent Application No. A 135/2013, filed on Feb. 22, 2013, the entireties of which are incorporated herein by reference.

The invention relates to an ECG device at least with limb electrodes.

Numerous attempts have already been made to record the mechanical activity of the heart and, respectively, the function of the vessels with external acceptors. A main reason for the fact that those methods have not widely been accepted is that they were not sufficiently precise and, at the same time, are not refunded by insurance companies and, respectively, that physicians hardly have the time for introducing additional unfinanced examination methods into their medical practice or into the hospital.

It is the object of the present invention to overcome the disadvantages of the lack of acceptance for the above examinations, their insufficient financial compensation by insurance companies and the amount of work additionally required from the medical staff by providing a multichannel ECG device by means of which, in addition to conventional ECG measurements, the mechanical activity of the heart and/or functions of vessels of the human body can be detected without any specific activities performed by the person in charge and unnoticed by the examined patient. In Patent AT 502921, a first step in this direction has already been taken, but the present invention provides further significant improvements over AT 502921. It is the objective of the present invention to use, if possible, only conventional ECG electrodes for many further purposes, for example, for a multi-frequency impedance analysis and its subcomponents effective resistance, reactive impedance and phase angle at different frequencies and, respectively, the change in impedance with the heart activity (e.g., z0, dZ, dZ/dtmax) and, furthermore, to use them for mechanical, acoustic, optical and temperature measurements and to get by with as few additional electrodes as possible. According to the invention, for example, phonocardiograms, apexocardiograms, pulse wave transit times, and/or pulse wave analyses are measured and recorded by means of sensors additionally attached to the electrodes. Furthermore, the measurement of the oxygen saturation, the circulation times such as, e.g., PEP, LVET, A2O and an accurate ascertainment of body compartments can be performed using a segmental impedance analysis etc.

The combination of a phonocardiogram sensor with a suction device has been known for decades (e.g., Bertrand C A et al. Circulation 8: 49-57, 1956), just as the combination of an ECG sensor with a phonocardiogram sensor has been known at least since 1986 (Little, U.S. Pat. No. 4,628,939, 1986). For example, an electronic stethoscope has also been described, with the electrodes for the ECG being located at the edges of the bell (Watson, US20010030077, 2001). In U.S. Pat. No. 7,110,804, Baumer describes a combined ECG electrode with a phono sensor in a cavity, using a conductive gel. In the application Bauer, WO 2006020764 A3, a suction cup is described in which an acoustic-to-electric transducer is positioned.

WO 2008/031030 (Bartnik) discloses the production of systolic time intervals by subtracting, from a first curve shape arising from an impedance signal, a second curve shape which is obtained by echocardiography or from the pulse wave or the pulsoximeter.

US 2005/0033190 (Bauer) describes a multiaxial accelerometer in an ECG electrode. US 2005/0273015 (Bauer) describes a vacuum chamber for a microphone of an ECG electrode. US 2009/0227886 (Bauer) describes a continuous "vibratory" stimulation near the resonance frequency of an acoustic sensor. The U.S. Design Pat. No. D675,738 describes an electrode design in which the microphone can be separated from an electrode.

WO 2006063255A2 (Bernstein) discloses the determination of the stroke volume from the impedance signal above the thorax or above the brachial artery.

US 2013/0096448 (Brooks) describes a combined ECG, ICG and phonoelectrode on a common carrier with an acoustic chamber. In contrast, no acoustic chamber is provided according to the present invention.

Documents U.S. Pat. No. 8,521,264 and US 2010/0324404 describe the use of a maximum number of three combined ECG-ICG electrodes which are all placed on the thorax.

U.S. Pat. No. 6,339,722 (Heethaar) suggests that the thorax be measured as a segment at two frequencies and with two different measuring distances in order to obtain information about the activity of the heart. In U.S. Pat. No. 6,560,481 (Heethaar), electrode positions for the impedance measurement above the clavicle and on the left side of the body underneath the sternum are described. In U.S. Pat. No. 7,904,141 (Osypka), LVET is calculated from two measurements of the impedance or from the applanation tonometry.

U.S. Pat. No. 4,807,638 (Sramek) and WO 89/03656 A1 suggest that the blood pressure be calculated with the aid of two impedance cardiograms above the heart and in the periphery.

In contrast to the above-mentioned publications, the present invention is based, relying on new physiological findings, on the use of a conventional multichannel ECG device and enables to conduct complex circulation and fluid analyses by means of at least one single electrode at the upper body aperture. The findings of the inventor imply, among other things, that the use of an impedance curve remote from the heart on a limb in addition to measuring the impedance curve on the thorax will enable much better the measurement of the cardiac output and the fibre voltage of the heart and, hence, will also be perfectly suitable for estimating biochemical parameters such as, e.g., a parameter of the BNP and derivatives thereof. Furthermore, the inventor has realized that measuring the impedance at at least two frequencies in segments of the body sequentially located close to the heart and remote from the heart provides an excellent parameter for a fluid overload or for a dehydration and that, by fragmenting the body into six segments, namely arms, legs, thorax and abdomen, the total body TBW, ECW and ICW can also be estimated excellently and that those parameters will contribute decisively to the measurement of the cardiac output and biochemical heart parameters. The thorax is referred to as a segment close to the heart, abdomen and limbs are referred to as segments remote from the heart. If thorax and abdomen are examined as a joint segment, they are considered as a joint segment close to the heart. Furthermore, the inventor shows that, from the relation of the % body fat or fat mass (FM) or % body water=total body water (TBW), as predicted on the basis of the segmental impedance, always based on the total body weight, or the "lean body mass" (LBM) to the ratio of extracellular water (ECW) to intracellular water (ICW), that is, to the ECW/ICW ratio or also to the ECW/TBW ratio, in a body segment or in the total body, an overhydration or underhydration of the body can also be identified for the first time. Furthermore, using the present invention, the parts of the body which are not passed through by an alternating current field are used as ion conductors, whereby a further simplification of the method and the electrodes used, specifically the clamping electrodes formed by two separate, but elastically joined branches, is provided.

In the following, the area of the neck, the back of the neck, head, shoulders and arms, preferably upper arms, as well as the electrode positions V1, V2 are referred to as the upper thorax aperture, and the area of the lower costal arch, xiphoid, i.e., the usual area for attaching the chest wall electrodes of the ECG, e.g., V4 to V6, e.g., V4 r to V6 r, as well as the boundary between the thoracic spine and the lumbar spine are referred to as the lower thorax aperture. The area of the pelvis, the buttocks and the proximal thighs are regarded as the lower end of the torso.

Below, the invention is explained in further detail on the basis of exemplary embodiments with reference to the drawings.

FIG. 3a shows an embodiment of an electrode in order to be able to record, besides the ECG, also the mechanical activity of the heart.

FIG. 3b shows a further embodiment of an electrode in order to be able to record, besides the ECG, also the mechanical activity of the heart.

FIG. 4 shows a suction electrode according to the invention.

Figure 8:
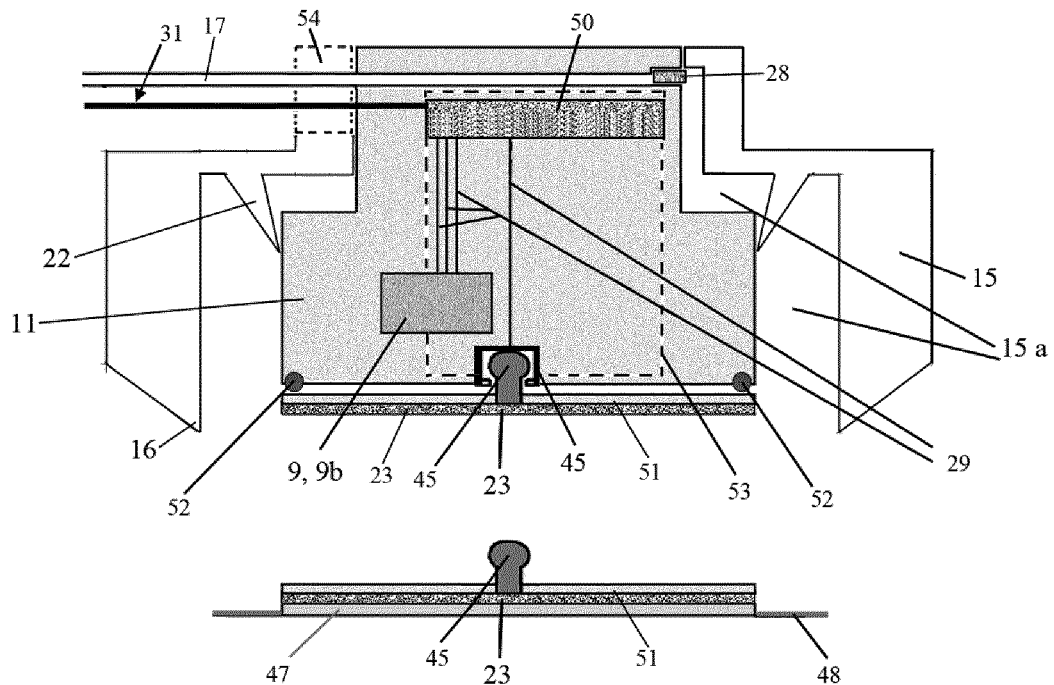

FIG. 8 schematically shows a universal electrode with a push-button connection—in the cross-section.

FIG. 9 to FIG. 13 show results of measurements on healthy and sick individuals, using the present invention.

Figure 1:
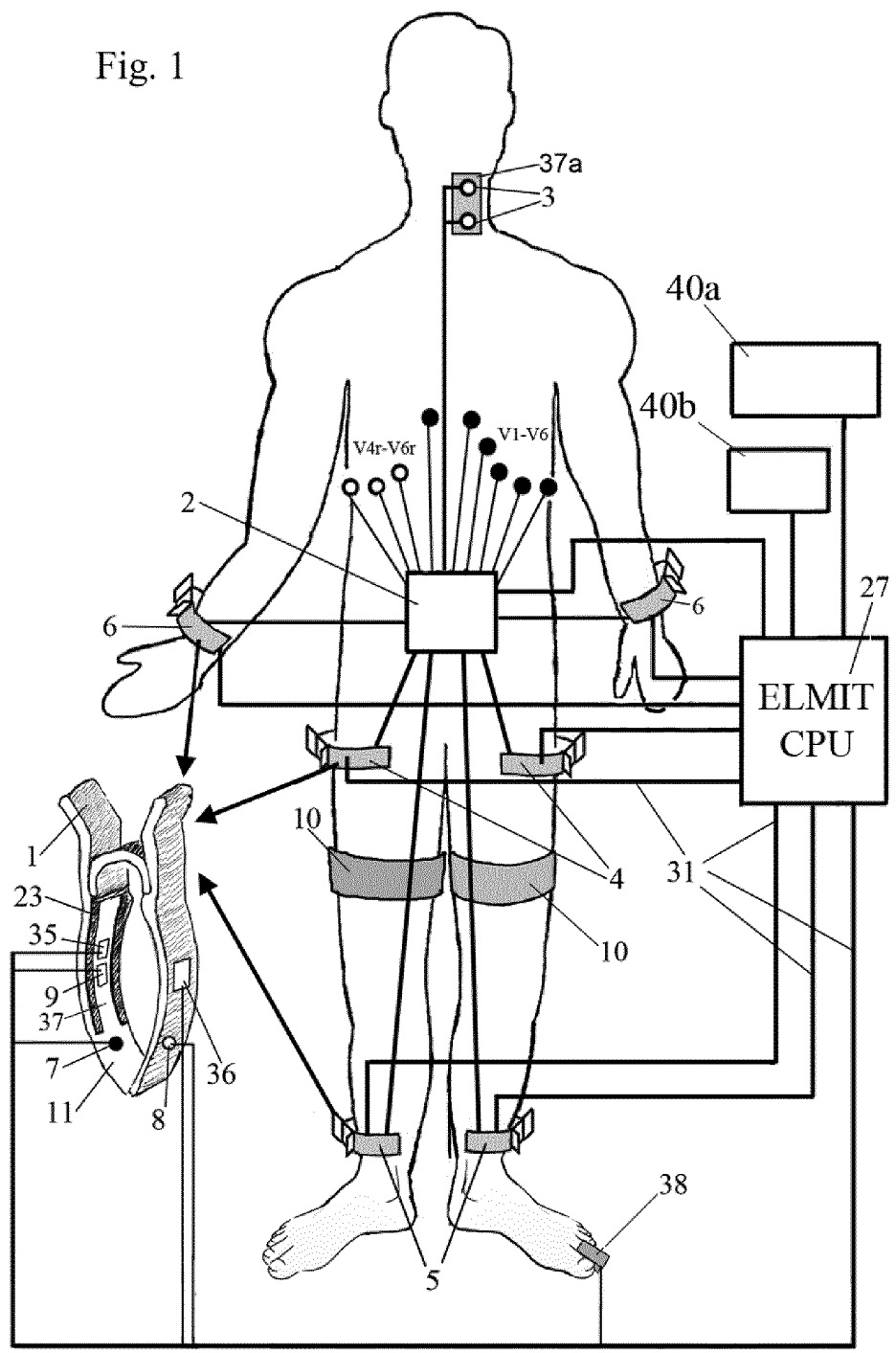
FIG. 1 shows the lead of a conventional multichannel ECG and an additional electrode.

FIG. 1 shows the leads of a conventional multichannel ECG consisting of the limb electrodes, herein, designed, for example, as a double electrode 1, e.g., as double clamping electrodes 1, and, on the other hand, as is known, of the chest wall leads (V1-V6, possibly supplemented by V4r-V6r), wherein, for examining the fluid equilibrium, the individual electrodes can be interconnectable by means of an electric or electronic switch 2, e.g., a multiplexer 2, or, respectively, can also be measured separately, or, respectively, can be developed as current supply electrodes and/or impedance measuring electrodes. In this connection, possible details of the arm electrodes 6, proximal leg electrodes 4 and distal leg electrodes 5 of one half of the body are configured as it is indicated with arrows in the detailed drawing of FIG. 1 on the left. For the sake of clarity, multiple electric lines 31 from the electrodes are drawn everywhere in the figures only as individual lines. By means of only one additional single or double neck electrode 3 and possibly by interconnecting, for example, V4 to V6, on the one hand, and V4r to V6r, on the other hand, e.g., by the multiplexer 2, the thorax can be examined closely with regard to its impedance (z0) and the fluid content and the change in the fluid content with the heartbeat (e.g., dZ, dZ/dt, dZ/dt max) using an impedance measurement. As is evident, the electrodes are not attached to the hands and feet, as customary, for instance, for impedance measurements, but to the distal forearm as well as to the distal shank. Double electrodes are convenient in particular for the four-point measurement of the impedance with externally located feeding electrodes and internally located measuring electrodes. The accommodation on a common carrier 37, 37a facilitates handling, but is not necessarily required. The current supply for that may occur, for example, between the upper thorax aperture, e.g., of a neck electrode (the back of the neck, or respectively, the head or, respectively, the shoulders might also be considered for placing the neck electrode) or, respectively, also the arm electrode/s 6, on the one hand, and the proximal leg electrode/s 4 and/or the distal leg electrode/s 5, on the other hand. Through the measured distance between the double neck electrode 3, on the one hand, and, e.g., from V4 to V6, on the other hand, the electric impedance or, respectively, the effective resistance and the reactive impedance of the left thorax can be examined, by establishing an interconnection, e.g., from V4r to V6r, a measured distance between the neck electrode 3 and the right half of the thorax can be achieved.

In this way, fluid accumulations in the left half of the thorax or, respectively, in the right half of the thorax, for example, due to a pleural effusion, or fluid accumulations in the area of the lungs, for example, as a result of pneumonia, atelectasis or a pulmonary edema, or, respectively, also the change in impedance caused by the heartbeat can be detected. Also, each of the chest wall electrodes can alone be used for measuring the impedance between the neck electrode 3, on the one hand, and one of the chest wall electrodes, on the other hand, only, the reproducibility of the measurement will then not be so good anymore. This is made up for if the electrodes, e.g., V4, V5, V6, are used individually for the measurement and, then, a possible averaging of the results occurs. Thus, the impedance of the entire thorax can be calculated mathematically also without an interconnection. Alternatively, one or several of the leads V1-V3 might also be used instead of the neck electrode for measuring the impedance between those leads and the leads V4 to V6, but the measured distance will then be very short and the signal-to-noise ratio will not be so favourable.

As mentioned earlier, the introduction of the current for the impedance measurement occurs in this case advantageously via one or both arm electrodes 6 and/or via the neck electrode 3, on the one hand, and either via one or both proximal leg electrodes 4 and/or else via the one or two distal leg electrodes 5 (either suction, adhesive, band or clamping electrodes) on the left and right legs, on the other hand, on the site where they are also used for the ECG leads. For separately examining the fluid or, respectively, the fluid shift in the two legs, the legs can be examined separately or jointly by an interconnection or separation in the multiplexer 2, or, respectively, the total impedance of the left and right legs can, also in this case, be calculated without an interconnection. Advantageously, the arm electrodes 6 are also designed, for example, as double electrodes 1, in the specific case as double clamping electrodes 1. However, the electrically conductive electrodes 23 do not have to be located on the same branch of the double clamping electrode 1 as shown in FIG. 1, but one of the two electrically conductive electrodes 23 could also be attached to the opposite branch of the double clamping electrode 1.

The additional measurement of the impedance change with the heartbeat in the limbs, arms or legs also enables a very good evaluation of the power of the heartbeat, in particular if this is used together with the impedance change on the thorax.

Also the patient's fluid equilibrium can be identified excellently with the above arrangement, since the body is divided into six sections, namely the two arms, the thorax and the abdomen, and, respectively, the two legs, by the additional neck electrode 3, the arm electrodes 6 and by the proximal leg electrodes 4 and the distal leg electrodes 5 as well as the chest wall electrodes V3-V6 and/or V3r-V6r. Also the wiring of the electrodes, which will be mentioned below in FIG. 2, enables the division into the six sections, also without using the proximal leg electrodes 4. The separation of the abdomen segment and the thorax segment for the body analysis is so convenient because they must be incorporated distinctly also in the calculation of the body composition, based on anatomical differences (e.g., the air-filled pulmonary alveoli). In each of those individual segments, the alternating current resistance (impedance) or, respectively, the effective resistance (resistance) and the reactive impedance (reactance) of the individual body sections is analyzed at several frequencies, possibly also a full frequency sweep, and the ECW, the TBW and hence also the ICW, especially also the ratio ECW/TBW or ECW/ICW, is analyzed therefrom. An analysis of the segments at at least two frequencies of, e.g., between 1 Hz and 10 Hz, e.g., 5 Hz, on the one hand, and at frequencies higher than 100 Hz, e.g., also of 400 or, respectively, 800 Hz, on the other hand, or also via a frequency sweep, has proved to be particularly useful, since, in this way, the ratio of the extra- to the intracellular fluid can be determined, which is independent of the dimensions of the examined segment. For measuring the impedance change with the heartbeat (dZ, dZ/dtmax), a frequency of about 40 kHz is usually used. This or a similar frequency should also be provided by the hemodynamic ECG device. The current supply for the individual segments occurs in each case, for example, through electrodes located outside of the examined segment, e.g., for measuring the thorax between the external one of the double neck electrode 3 or, respectively, the head electrode or, respectively, the arm electrode/s 6, on the one hand, and one of the electrodes located distally to the chest wall electrodes, e.g., the proximal 4 or distal leg electrodes 5, on the other hand, for measuring the abdomen segment through a supply at the arm electrodes 6 and/or neck electrodes 3, on the one hand, and the distal leg electrodes 5, on the other hand, for measuring the arms through a supply at the distal double arm electrodes 6 and the neck electrode 3. The measured thorax segment is located between the proximal neck electrode, on the one hand, and one or several chest wall electrodes V4 to V6 or, respectively, V4r to V6r, on the other hand. For measuring the impedance change with the heartbeat on the thorax, the proximal leg electrodes 4 may also be used, since the abdomen does not contribute to the dZ/dt. Further simplifications such as, for example, the construction of the proximal leg electrode 4 as a single electrode, are also envisaged. Of course, the usual defibrillation protection has also been borne in mind Since the measuring module is supposed to be located close to a central rod to which the extension arm with the patient cables is mounted, the patient cables should run along the extension arm and, at the end thereof, should dangle freely for use. In order that they do not become entangled, it is suggested that a spacer be provided at the end of the extension arm, which spacer spatially separates the patient cables depending on their positions on the body.

Further simplifications are also provided, for example, a specific simplification of the measurement, wherein the two electrodes on the thighs may then be omitted and the body can still be analyzed exclusively with the electrodes of the limbs and the thoracic wall in 6 segments, namely the thorax, the abdomen and 2 legs and arms each. In many cases, single electrodes, for which, for example, the ECG electrodes may be used, will then be sufficient at the measuring points, namely if the supply of the current occurs elsewhere.

Figure 2:
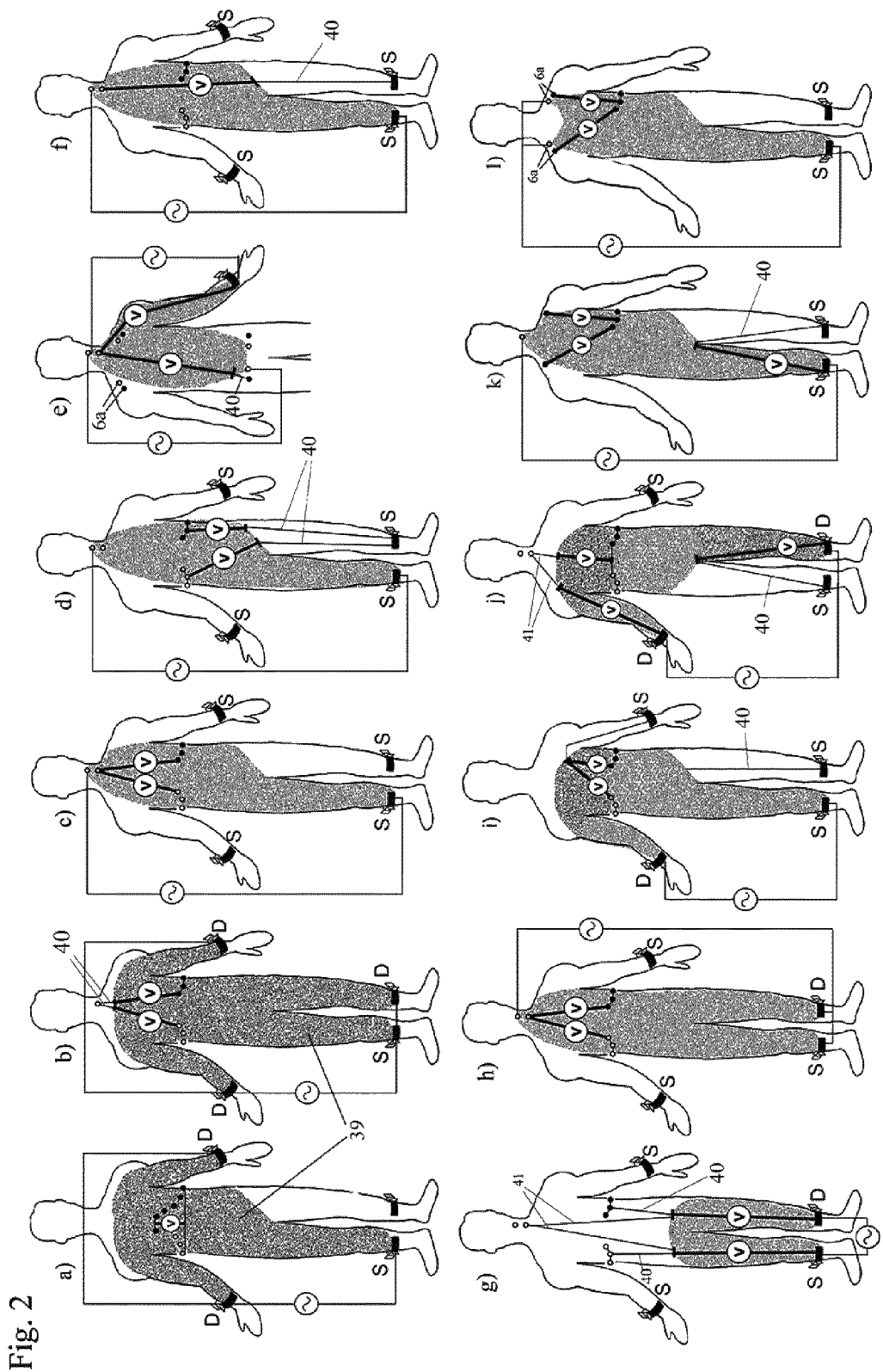
FIGS. 2a to 2l show the respective localizations of the current supply with an alternating current source and furthermore, in a very schematic way, the electric fields thus building up in the human body.

In FIGS. 2a to 2l, the respective localizations of the current supply are depicted with an alternating current source, and, furthermore, in a very schematic way, the electric alternating current fields -39-, which are thus building up, as dotted areas. The measured distances are also indicated with the usual symbols, herein, for example, with V. In this connection, it is indicated in the respective partial figures a-j as to whether, as a minimum requirement, there is a double electrode, symbolized by D, or a single electrode, symbolized by S, in the respective figure. Parts of the human body in which no current field has built up are thereby used only as an electrical conductor 40, more precisely as an ion conductor 40, since the body's electrolyte content with its high extracellular and intracellular ion concentration constitutes a good conductor especially for alternating current. In this connection, it may prove to be useful to use something higher than the commonly used 40 kHz also for measuring the impedance and its change with the heartbeat in order to safely ensure a conduction of the alternating current also through the intracellular water. FIG. 2 shows further possible current supply localizations and localizations for calipering the impedance, with the ECG electrodes being used preferably as far as possible. For example, the ground electrode (usually as a black electrode on the right leg), on the one hand, and one of the two arms or both arms, on the other hand, may be used for the current supply (FIG. 2a). The ground electrode can be used readily for this, whereas a double electrode proves to be useful for the arms, since the ECG lead electrodes on the arms should not be used for supplying the current (FIG. 2a). By contrast, the ECG electrodes may be used for measuring the impedance or, respectively, their subcomponents resistance and reactance. Herein, only the impedance is always mentioned, even if the subcomponents and the change in impedance with the heartbeat (dZ, dZ/dt max and further characteristics) may be meant by this. For example, the impedance between the neck electrode 3 and the electrodes not used for the interconnection as a central terminal according to Wilson, namely one of the electrodes V1 to V6, e.g., V4 to V6, may be used for measuring the impedance and/or its change with the heartbeat, wherein, in this case, the supply occurs, for example, via both arms and both legs (FIG. 2b), for which one leg and one arm might also be sufficient. The impedance between the individual chest wall electrodes, i.e., those which cannot be interconnected for Wilson's central terminal, may also be measured. For example, this could be between V1 and V6 (possibly also V4 or V5) or also between V1, V2, optionally interconnected, on the one hand, and V6,V6r (possibly also V4 or V5 with V4r and V5r), optionally interconnected, on the other hand (FIG. 2a). In this case, the electrodes V1, V2 would be allocated to the upper thorax aperture. The right ventricular leads are only an additional option, a full analysis of the heart activity and the fluid distribution in the body can also be performed without them. The right ventricular leads have the advantage that the left thorax can be compared to the right one with regard to the impedance and that, at the same time, the diagnosis of a posterior myocardial infarction in the ECG is facilitated. Additional leads such as Nehb leads or Frank leads are likewise possible.

These are only examples, the interconnection of other electrodes not interconnected in Wilson's central terminal is also envisaged. Using only one single further electrode which is located between two of the electrodes provided for Wilson's central terminal, namely between the left and the right arm electrodes 6, Einthoven Lead I (the electrodes red and yellow of a conventional ECG), the impedance and its change with the heartbeat could be measured particularly accurately, since the measured distance becomes longer and hence the signal-to-noise ratio becomes better. This electrode would finally be located at the neck 3, the back of the neck, the upper thorax aperture or the cranium. Possibly by using a double electrode 3 at this localization, not only can the current be supplied, but the impedance can be calipered as well (FIG. 2c). For measuring the thorax segment, the supply could occur, on the one hand, at the outer neck electrode and/or at the arm electrodes 6 and, on the other hand, if provided, at the proximal leg electrodes 4 or distal leg electrodes 5, the measurement of the voltage could occur between the inner neck electrode and the chest wall electrodes, whereby the left and right thorax should be measured as a whole by interconnecting, e.g., V5; V6, V5r and V6r and/or also only on the right and on the left, for example, via V4-V6, on the one hand, or via V4r-V6r, on the other hand (FIG. 2c). For measuring the thorax segment, it is not essential whether the current is supplied only via the ground electrode (black, on the right leg) or via both legs, namely the ground electrode and that of the 3 electrodes which is interconnected for Wilson's central terminal and is not used for Lead I according to Einthoven. The reason for this is that the current field in the torso is already extremely homogeneous even if the supply occurs only through one leg (FIG. 2c). The measurement of the thorax could also occur through a supply on one arm, on the one hand, and one or both legs, on the other hand, the measurement of the voltage could occur between the respective contralateral arm and the chest wall electrodes (FIG. 2i) or, respectively, if provided, at the proximal leg electrode/s 4, on the other hand. In this case, the contralateral arm in FIG. 2i would act only as a current conductor. By contrast, the measurement of the dz/dt on the thorax is inconvenient between the neck electrode 3 and the distal leg electrode/s 5, since a differentiation between the volume change with the heartbeat at the thorax and that in the limbs will then not be possible. However, the measurement of the volume change, e.g., dZ/dtmax, at the thorax and at a limb is particularly suitable for evaluating the cardiac output, especially if, in addition, the ratio of the extra- to the intracellular fluid is taken into account. From those three combined parameters, a limitation or improvement of the cardiac output can be detected particularly well.

For measuring the abdomen, for example, the current supply between one of the two or the two arm electrodes 6, on the one hand (alternatively, the neck electrode/s, on the one hand), and one of the distal leg electrodes 5, on the other hand, is possible, the impedance measurement between, for example, one or several interconnected chest wall electrodes, on the one hand, and, if provided, the respective contralateral proximal leg electrode 4 or, respectively, distal leg electrode 5, which is not envisaged for the current supply, on the other hand, is possible (e.g., FIG. 2d). For measuring the abdomen, the current supply occurs, for example, between one of the legs and one or both arms, and the measurement of the voltage occurs, in each case, between the contralateral leg and the chest wall electrodes.

For measuring a leg segment, the current supply occurs, for example, always between the external ones of the two distal leg electrodes 5, and the impedance measurement occurs, in each case, between the inner distal leg electrode 5 of the examined leg, on the one hand, and the chest wall and/or neck and/or arm electrodes 6, on the other hand (e.g., FIG. 2g). Furthermore, for measuring the arms, the current can thus also be supplied between the outer arm electrode 6 and the outer neck electrode 3 and the voltage can be discharged between the inner neck electrode and the inner arm electrode 6 (FIG. 2e). This applies in a mirror-imaged and analogous manner to the measurement of the left arm, wherein, naturally, other supply points are possible as well. A further measurement of the arm and the thorax is illustrated in FIG. 2j. A further simplification is created possibly by omitting also the neck electrode: For the purpose of measuring the arm segments, the supply would have to occur between both arms, and, for analyzing the arm of interest, the voltage would have to be measured between said arm, on the one hand, and the chest wall electrodes V4 to V6 or, respectively, V4r to V6r and/or the proximal 4 or distal leg electrode/s 5, on the other hand. It is obvious that a combination of the different FIGS. 2a to 2l is possible. A particularly practical and preferred form is possible by combining the supplies of FIGS. 2g and 2h, if proximal leg electrodes 4 are to be omitted. In doing so, the neck electrode or one or several chest wall electrodes may be used alternatively for measuring the legs, as shown in FIG. 2g. In FIG. 2g, the arms could also be used together with the legs for the impedance measurement of the legs (not illustrated). On the other hand, it might also be possible to supply the alternating current between a distal leg electrode 5 and one of the electrodes located in the upper half of the body and to measure the impedance between the distal leg electrodes 5, whereby only one leg would then be passed through by the alternating current and the other leg would be used as an electric ion conductor 40 (FIG. 2 j and FIG. 2 k). In this way, it is possible exclusively with the aid of the limb electrodes and the chest wall electrodes with or without a neck electrode to analyze each one of the six segments. However, the precision of the measurements is improved further by additionally using the neck electrodes 3 and additional proximal leg electrodes 4. For the initial examination, particularly the complete ECG with chest wall electrodes and limb electrodes is of interest, in the absence of heart complaints, it will perhaps subsequently be possible to get by with the information with the limb leads. Thus, the dz and dz/dt of the segment close to the heart can be measured if the current is supplied between the electrode at the upper body aperture (e.g., the neck electrode 3, the shoulder electrodes 6a) and a distal leg electrode and the impedance is measured between the neck electrode and the distal electrode on the other leg (FIG. 2f). The dZ and dZ/dT at the body segment remote from the heart is measured if the current is supplied between the two distal leg electrodes and the impedance is measured between the electrode at the upper thorax aperture or a chest wall electrode, on the one hand, and a distal leg electrode, on the other hand (FIG. 2g). If the limb electrodes for Lead I according to Einthoven between the right and the left arms are designed as shoulder electrodes 6a, those electrodes can also assume the function of measuring the impedance at the upper thorax aperture and the neck electrode 3 can be designed only as a single electrode for the current supply and, respectively, the distal arm electrodes may naturally be omitted (FIG. 2k), whereby an analysis of the arms will then not be possible anymore, said arms constituting only about 7% of the body volume. This arrangement is particularly reasonable especially also for the ergometer load. FIG. 2 *l* shows a placing of double electrodes (e.g., adhesive or suction electrodes) at the upper thorax aperture, namely on both shoulders, via which, on the one hand, the ECG writing of the limb leads may occur and, on the other hand, the current for the impedance measurement can also be supplied at those places. This would be one of the versions with minor changes in comparison to the conventional ECG. A combination of the different variants of FIGS. 2*a* to 2*l* is, of course, envisaged. In this connection, it must also be emphasized that the results of the impedance measurements depend critically on the positions of the current supply and the voltage measurement, for which reason double electrodes on a common carrier are advantageous. It must also be emphasized once more that it is advantageous not to interconnect the electrodes, e.g., the chest wall electrodes, but to measure, for example, the impedance and its change with the heartbeat from the neck toward V4, V5 and V6, in each case, separately, even if always only a portion of those measured distances is depicted in FIG. 8 for the sake of clarity, and then to obtain even more accurate results by averaging the measurements. The limb leads (instead of the arm and leg electrodes) can be implemented with up to 4 double electrodes or else single electrodes on the back, as depicted in FIG. 2*e*, especially for the ergometry, and, at the same time, the change in the thorax impedance with the heartbeat (dZ and dZ/dtmax, respectively) in order to thus detect the change in the heart acceleration under ergometry, as it is caused primarily by adrenaline. In this way, the sensitivity of the conventional ergometry can be increased further, namely if an increase in the dZ or dZ/dtmax is less pronounced than in a healthy person. The chest wall electrodes which should continue to be applied for the ergometry are, of course, not visible in this rear view of FIG. 2*e*. If a feeding electrode is used on the neck, a double electrode at the lower end of the back is sufficient as a minimum, if the neck electrode for the supply is missing, one or two double electrodes at the upper thorax aperture on the back may also be used for this purpose. Thus, the arms and legs are free to move. The measurement of an arm is also depicted in FIG. 2*e*, wherein this will not occur simultaneously with the measurement of the back.

In the described figures, for example, the principle of a four-point measurement with externally located current and internally located voltage electrodes is implemented, with a two-point measurement also being envisaged. It should also be made understandable that the indicated examples can be modified further and that whenever the dissipation of the impedance occurs remote from the impression of the current, it is understood that single electrodes will be sufficient at the respective impression or dissipation positions. Also a combination of different supply points, e.g., neck and arms, would render the current fields e.g., on the thorax even more homogeneous. It is also obvious that the current fields cannot be as homogeneous as depicted.

As shown in FIG. 1, FIG. 3 to FIG. 8, it is possible to accommodate also additional sensors such as, e.g., temperature sensors 35, or also light sources 7, e.g., LEDs and light sensors 8, on all electrode bodies 11, namely on the electrode body 11 of the clamping electrodes 1, the elastic suction cups 15 or the adhesive electrodes 46. The LEDs 7 could be attached, for example, opposite to the light sensors 8, e.g., at the opposite branches of the clamping electrode (FIG. 1). The light sources 7 and the light sensors 8 could also be located side by side, and the reflection of light through the arterialized blood and the pulsation thereof could be measured. Also in this case, there could be suction electrodes, on the one hand, and, on the other hand, clamping electrodes or elastic straps might also be used for fixing the electrodes in a known manner. This applies to Electrodes I, II and III, as they can be interconnected to Wilson's central terminal, and to the ground electrode, respectively. Also in this case, mechanical sensors 9, e.g., the accelerometer 9*b*, may prove to be useful, for example, in order to record the shock wave of the blood, the blood flow and the volume change with the heartbeat also outside of the thorax and also the pulse wave simultaneously with recording the change in z0, dZ and dZ/dt max. In this way, for example, circulatory disorders can be detected easily and, respectively, the pulse wave velocity between the individual electrodes can also be measured. If the mass of the electrode body 11 is small, such as, e.g., in case of chest wall electrodes, the accelerometer can, for example, be fixedly connected to the electrode body 11, if the electrode body 11 is large, such as, e.g., in case of clamping electrodes 1, it may be advantageous to mount the mechanical sensor 9 movably on the electrode, for example, via a membrane 13. It is understood that this problem does not arise in adhesive electrodes 46, e.g., in a spot-adhesive electrode 46 or in a band-adhesive electrode or in an electrode kept low with an elastic band, since the mass of the electrode body 11 is small in the first place. With temperature sensors 35, for example, temperature differences between the different electrode positions, as they may be caused, for example, by circulatory disorders, may be detected automatically. With position sensors 36, e.g., on an electromagnetic basis, or, respectively, with a measurement of the transit time or, respectively, radio interferometry, or, respectively, triangulation, the distance between the individual sensors or their positions in space could thus also be detected. The distance, for example, from the neck electrode 3 or the chest wall electrodes V1-V6 or V1-V6r to the proximal leg electrode 4 or, respectively, the distal leg electrode 5 would be of interest in order to thus automatically detect the pulse wave transit time of the mechanical sensors 9 or the volume wave transit time with the aid of the impedance measurement or the blood flow transit time by means of the light sensors 8, and, respectively, the distance measurement also assists in the normalization of the impedance values to the length of the segment.

By additionally attached inflatable cuffs 10, in which the pressure can be changed, in particular constrictions or obstructions in the bloodstream can thus also be identified, wherein, for example, if a constriction is present in the bloodstream, the pulse wave or the volume wave appears only at cuff pressures which are lower than in the healthy state. All those recordings take place during the implementation of a normal ECG and also within the same time, thus, an additional large amount of information about the mechanical heart activity and the function of the vessels, respectively, could be obtained, for example, during the recording of the rhythm strip. All the indicated electrodes may be designed as adhesive electrodes 46, suction electrodes or clamping electrodes or, respectively, may be fixed to the body with an elastic band. For example, the neck electrode in FIG. 1 is designed as a double spot electrode 3 on a common carrier 37, for example, of a common adhesive film 37*a*. If the neck electrode 3 is attached above the jugular vein, a venous pulse curve can also be recorded, which proves to be useful, for example, in case of heart failure and pericarditis. Also several interconnected spot electrodes could easily be attached on the neck on the left and on the right. In case several sensors are attached to the electrodes, several electric supply lines, possibly also screened supply lines, to the electrodes would possibly also be required, which might restrict the movability of the cables. In order to prevent this, the obtained signals could be transmitted to ELMIT 27 and the CPU 27 for further evaluation also via radiocommunication. It is also envisaged that additional sensors can be attached also outside of the ECG electrodes. It is thus envisaged that a light emitter and light sensor, e.g., in the form of a pulsoximeter 38, is attached to at least one of the acra, thereby analyzing the oxygen saturation and the pulse wave, for example, also the shape of the pulse wave. In combination with the at least one inflatable cuff 10 placed on the arm, thigh or shank, the blood flow or, respectively, a disorder thereof can thus also be analyzed in various limbs, for example, in a known manner also in the form of the ankle-brachial index.

A further improvement of the conventional ECG is achieved in that one or several electrodes at the thoracic wall, i.e., electrodes not interconnected for Wilson's central terminal, is/are suitable also for the recording of a phonocardiogram or, respectively, mechanical excitations. A left lateral position of about 30 degrees proves to be useful for an optimum signal, which can be facilitated, for example, by a wedge cushion.

In this context, it is shown in FIG. 3 how those electrodes must be designed in order to record, in addition to the ECG, also the mechanical activity of the heart: With 11, an electrode body 11 is characterized, which is, for example, roughly circular or oval-shaped and in the interior of which a mechanical sensor 9, e.g., an acceleration sensor 9b, is accommodated, for example, symmetrically or asymmetrically. Said mechanical sensor 9 may be, for example, an accelerometer 9b, which may be covered completely by the continuous electrically conductive electrode 23, as shown in the upper part and in the lower part of FIG. 3. On the other hand, the mechanical sensor 9, e.g., the accelerometer 9b, might also be attached to a flexible membrane 13 with as little attenuating effect as possible, for example, within the opening 24 of the electrically conductive electrode 23 so as not to experience an attenuation by the mass of the electrode body 11, as shown in the right-hand centre of FIG. 3. Said accelerometer 9b is able to record the pulsation of the heart such as, e.g., the apex beat of the heart, the apexogram, or also the sound vibrations originating from the heart such as, e.g., the heart sounds and the cardiac murmur. In case several mechanical sensors 9 are attached within the different chest wall electrodes V1 to V6, decelerations in the movement of the heart from one heart sector to another may also be recorded, as they may develop, for example, as a result of non-functioning areas of the heart, e.g., following a heart attack. In order to be able to use the mechanical sensor 9, e.g., the accelerometer 9b, for a phonocardiogram and for recording the movement of the heart, at least one electronic filter should be provided for processing the signal. For recording the phonocardiogram, a high-pass filter is suitable which lets through frequencies of between about 50 to 70 Hz, preferably about 70 Hz, on the one hand, and about 1000 Hz, on the other hand, and for use, for example, in the apexogram, a low-pass filter is suitable which lets through frequencies of between about 0.1, on the one hand, and about 20 to 70 Hz, preferably about 30 Hz, on the other hand. A parallel design of at least two electronic measured distances is particularly advantageous so that both frequency portions can be reworked in parallel and possibly differently. Thus, the systolic and diastolic time intervals such as, for example, PEP, LVET as a measure of the systolic function, e.g., A2O as a measure of the disastolic function, and a third heart sound as it occurs in case of heart failure can be observed simultaneously, and, respectively, a characteristic cardiac murmur as it occurs in vitia can be detected from the apex cardiogram and the phonocardiogram.

If an accelerometer 9b is used, the opening 24 in the electrically conductive electrode 23 may be omitted, since the acceleration is passed on to the mechanical sensor, e.g., the accelerometer 9b, also through the electrically conductive electrode 23. It is envisaged that this electrode body 11 is attached to the body either by means of an adhesive film (not illustrated, as this is standard) or possibly in a known manner by means of a suction electrode, wherein an elastic suction cup 15 is depicted with 15, which forms a tight lip 16 around the electrode body 11 on the examined body so that a vacuum can be produced within the suction electrode.

In order to obtain the best possible signals, a vacuum completely devoid of vibrations is very advantageous. The elastic suction cups 15 are connected to the negative pressure source 18, e.g., of a suction pump via suction lines 17, wherein the negative pressure source 18 either can be devoid of vibrations in the first place, which might be the case, for example, in a vacuum tank of a large capacity, or at least one strongly attenuating equalizing vessel 19 of an appropriate size or several equalizing vessels 19, possibly connected in series, is/are provided. Possibly, there are, in addition, valves 20 between the elastic suction cups 15 and the equalizing vessel/s 19 which open up only if the vacuum pump is not activated. Thus, a negative pressure absolutely devoid of vibrations can always be generated, wherein, for example, also the signal quality of electrical and mechanical and optical acceptors might have the optimum negative pressure adapted in a regenerative way. In doing so, the negative pressure can be adjusted such that, under said pressure, the signal quality and the signal-to-noise ratio of electrical, optical, mechanical and temperature sensors 35 are optimal. A drain valve 21 for quickly eliminating the vacuum may be provided, and, of course, it may be combined with the valve 20.

In order to make sure that the negative pressure in the electrodes not applied to the body is not lost, the suction electrodes are designed such that a negative pressure can develop only in the state of being applied to the body in the suction chamber 15a, which arises between the electrode body 11 and the elastic suction cup 15, if the electrode body 11 is applied to human or animal skin. For this purpose, it is necessary to press the electrode against the body, whereby a sealing lip 22 opens up between the electrode body 11 and the elastic suction cup 15, as described already in 1984 (Lundbaeck, U.S. Pat. No. 4,646,747, 1984). As soon as the electrode is removed from the body, the sealing lip 22 closes around the electrode body 11 due to its inherent elasticity and the negative pressure remains in the suction line/s 17 of the applied and non-applied electrode/s.

If the electrically conductive electrode 23, e.g., a silver chloride electrode, has a, for instance, asymmetrical opening 24 for the mechanical sensor 9, e.g., a microphone 9a or an accelerometer 9b, this involves the advantage that a larger closed electrode surface for the electrical contact with the skin is provided. On the other hand, the mechanical sensor 9 can be placed on the body without a change in the position of the electrode only by a rotation in such a way that the mechanical sensor 9 ends up lying between the ribs of the human body, even if the main part of the elastic suction cup 15 ends up lying above the ribs of the human body. By placing a further mechanical sensor 9 in a further electrode on the thorax at a spot where cardiac sounds or heart movements do not occur, e.g., V4r to V6r, the background noise or the background movement on the thorax could also be recorded and the useful signal for this disorder might be corrected.

The electrode body lines 29 from the electrically conductive electrode 23 or, respectively, the mechanical sensors 9 and/or the temperature sensors 35 run either, for example, to a female connector 26, e.g., to a female multipole connector 26 and via the respective contacts 30 to a connector 25, e.g., a multipole connector 25, or also directly to the combined ECG, light, mechanical and impedance and temperature analyzer, abbreviated with ELMIT 27, or, respectively, to the CPU 27. For the sake of clarity, the electric lines 31 are identified in many cases only as single lines, even if more than one electric line 31 is required for the function, and, also, not all lines are indicated with 31, since the electric connection between the individual elements is apparent in the figure. In order to make sure that residues from the skin such as sweat, hairs or cutaneous scales do not get into the suction lines 17, an air-permeable thrush 28 is provided which prevents biological residues and moisture from passing through and which can be replaced after the elastic suction cup 15 has been turned away. The contacting of, for example, the multipole connector 25 via the female multipole connector 26 toward the electrode body lines 29 within the electrode body 11 constitutes a challenge since the elastic suction cup 15 and hence also the electrode body 11 and hence also the multipole connector 25 must be relatively small so that a proper negative pressure can be built up. Nevertheless, the electrical safety distances as required by law must be kept between the contacts 30. Therefore, it is suggested that an electrically conductive pipe 32 is mounted around the multipole connector 25, which pipe serves as an additional electrical contact and, at the same time, also serves as a transport medium for the negative pressure and seals the suction lines 17 toward the elastic suction cup 15, thereby allowing the elastic suction cup 15 and/or the electrode body 11 to be replaced easily. In doing so, the electrically conductive pipe 32 is separated from the multipole connector 25, for example, by an insulator 33. Of course, it must be made sure that the vacuum within the pipe is in communication with the suction line 17 within the elastic suction cup, which becomes possible, for example, via a bore 34 in the insulator 33. In the lower part of FIG. 3, the electrode body 11 is depicted as rotated by 90 degrees so that the form of the suction line 17, the multipole connector 25 and the female multipole connector 26 with the contacts 30 become better visible therein. The electrically conductive pipe 32 is drawn in a dashed way, since it is not located in the sectional plane of the figure. If the electrode is developed only as an electrically conductive electrode 23 without any additional sensors at the electrode body 11, a multipole connector 25 is, of course, not required, but only a singly contacting connector 25. The connector 25 and the female connector 26, respectively, serve for allowing the elastic suction cup 15 to be replaced easily as well. The connector 25 and the female connector 26 might also be located anywhere in the electric line 31 to the electric or electronic switch, e.g., multiplexer 2. However, in this case, the connectors 25 must also be designed so slim that the electric lines 31 can be threaded from the elastic suction cup with the connector 25 or the female connector 26 jointly with the electrode body 11, which, in this case, is fixedly connected, that is, that the suction cup alone or, respectively, the electrode body 11 alone with the cable attached thereto can then be replaced easily. That is to say, the outer diameter of the connector 25 then also must not be substantially larger than the recess 15b in the elastic suction cup 15, into which the electrically conductive pipe 32 is introduced in FIG. 3.

It is envisaged to generate and store templates (models) of all measured and calculated parameters during phases of an unchanged heart activity. If the examination is then repeated at a later time, the changes in the parameters can be recorded numerically and graphically as a trend. For this purpose, it is also envisaged to use standard panels for the individual parameters. If, during a single examination, several examination periods are linked together, for example, after physiological or pharmacological interventions and, for instance, several templates of the same parameters are generated, the temporal pattern of the change in the cardiovascular activity can be analyzed and the trend can be recorded. If the examination is then repeated after some time, the trends of the individual examinations, which have taken place at a different point in time, could then be overlaid, illustrated graphically with date information in order to thus easily identify changes in the cardiovascular activity between the individual times of the examinations. Also in this case, it is envisaged to use standard panels for the individual parameters. Examples to be mentioned are changes in the ST distance or in the dz/dt during an exercise stress test. The signals for the beginning and the end of the periods can be entered either manually or also from a different device, e.g., from an ergometer. Specifically, it is also envisaged to analzye alternative heartbeats in separate templates in order to thus generate and analyze not only the "electrical alternans", but also a "mechanical alternans" in order to thus be able to identify a dysfunction of the myocardium even better. The measurement of the change in the volume not only in the thorax, but also at at least one limb (dZ or dZ/dt) also enables the determination of a concordant or discordant alternans of the right and left ventricles, since the change in the volume in the thorax with the heartbeat is caused primarily by the right ventricle, in the limb, however, only by the left ventricle. Specifically, extrasystoles which have been detected will also be used for finding an alternans subsequently triggered thereby. For triggering an alternans and also for a general analysis of all signals such as, e.g., heart time intervals, pulse wave transit time, volume acceleration by dz/dt etc., the use of stimulation methods for the circulation such as, e.g., an increase in the heart rate by physical work or pharmaceuticals and, respectively, during the recovery phase from those stresses has been considered, since, in this way, an even better evaluation of the circulation becomes possible.

All data obtained can be stored permanently in a memory 40a allocated to the patient. Thus, the patient can be examined over time in longitudinal section examinations and changes in comparison to previous findings can be recorded and identified and, respectively, can be issued in the findings in the form of numbers or graphically, for example, by the printer 40b. Of course, this applies not only to the electrical activity such as changes in the P wave, R spike and T wave vector, anomalies in the p wave, the chamber complex and the fluctuating repolarisation, the PQ time, the duration of the chamber excitation, the height of the T wave, the QT duration, the QT dispersion and other changes in the ECG, in addition, changes in the impedance with the heartbeat and all other above-indicated parameters such as, e.g., cardiac output, heart failure class (e.g., NYHA class), estimated atrial natriuretic peptide, e.g., BNP, NT-proBNP, the soluble ST2 receptor (sST2), cardiotrophin, adrenomedullin and/or other estimated biochemical parameters for the fibre voltage of the myocardium and, respectively, for biomechanical stress, systolic function, diastolic function, heart valve defect, extracellular water, intracellular water, total body water, muscle mass, fat mass, extracellular/intracellular water ratio and, respectively, the distribution of the body water and subcomponents thereof and their ratio to each other in the individual body parts are also identified in this manner and output as numerical values and/or graphically as a trend over time so that a threat to the patient as a result of a change in the above parameters can be detected at a glance. Then, the obtained crude data must be processed partly by being combined with each other in complex calculations, e.g., multiple regression equations, in order to calculate the desired parameters. Examples to be mentioned are only the combination of changes in the dZ/dt max in different body segments with a detection of an expanded extracellular water (ECW), e.g., of an increased ECW in relation to the intracellular water (ICW) or in relation to the total body water (TBW), i.e., an increased ECW/ICW or ECW/TBW ratio, or also a change in the apexogram curve together with a change in the systolic and diastolic time intervals, for example, also the fast relaxation time, namely the A2O time for detecting a disturbed diastolic function, as they can be determined by detecting heart sounds and from the apexocardiogram. The changes in the apexocardiogram such as, e.g., a "mid systolic bulge" can also be used in addition to the ECG changes for diagnosing a heart attack. Defects in the pericard, e.g., pericarditis, and, respectively, also heart valve defects, e.g., aortic stenosis, can also be identified based on the relation of the a to the e-o waves in the apex cardiogram. Also, the first derivation of the apexocardiogram enables a particularly precise evaluation of the cardiac function. But also the training state and an improvement in the cardiovascular performance can be calculated readily from the indicated parameters via regression equations also without a maximum load, thus, for example, VO2max, the maximum wattage to be accomplished and the physical performance can be estimated in percent of the standard, for example, by means of multiple regression equations and, respectively, also neural networks, which is helpful in the training counselling of athletes and sick people. A change in the muscle mass in individual body segments and in the total body can also be detected by means of the obtained data.

For detecting an over- or underhydration, the calculation of the deviation of the TBW or ECW or ICW or ECW/ICW ratio from the regression line determined between the FM/kg body weight, on the one hand, and the TBW/kg body weight or, respectively, the ECW/kg body weight or, respectively, ECW/ICW in healthy persons proves to be particularly useful. In order to optimize the signal quality of all signals, it is also envisaged, on the one hand, to amplify the signals as close as possible to the sensors, for example, in a known manner with operational amplifiers, which compensate possible interspersals and falsifications, respectively, furthermore, all lines should be equipped with active screens when necessary, moreover, an early digitization of the signals close to the sensors is also envisaged when necessary, which would help to eliminate possible problems with the signal quality.

FIG. 4 shows another embodiment of the suction electrode, wherein two different connectors (=plug connections) 25, 44 receive the contact with the electrically conductive electrodes 23 in the electrode body 11 surrounded by the elastic suction cup 15. Namely, for safety reasons, a large safety distance as specified in the standards must be kept between the electrode body lines 29 leading to the electrically conductive electrode 23 and to the mechanical sensor 9, which otherwise can hardly be realized. Whenever a connector and a female connector are mentioned in this application, any person skilled in the art will understand that the two terms are meant to be exchangeable, for which reason the term plug connection 25 is introduced.

For example, a conical connector 43 establishes the electrical contact to the female connector 26. A large-scale design of the conical connector 43, for example, with a gold-platet surface ensures a good electrical contact also in case of a corrosion of the conical connector 43 caused by humidity. A bore 34 in the electrically conductive pipe 32 thereby establishes the connection to the suction chamber 15a. A second connector 44, e.g., a jack plug, with several contacts 30 to the female connector 26 is mounted, for example, in the electrode body 11 and establishes a connection to the mechanical sensor 9. Two recesses 15b in the elastic suction cup 15 seal the lead-through of the two connectors 25, 44 toward the suction cup 15. Any person skilled in the art will understand that, instead of the second connector 44, a female connector 26 might also be mounted in the electrode body 11 and the second connector 44 could be introduced into the suction cup 15 through the recess 15b. However, the design which is actually shown has the advantage that, in case of a replacement of the suction cup 15, the second connector 44 may serve during the introduction of the electrode body 11 into the elastic suction cup 15 for guiding the former through the recess 15b. A comparison between FIG. 2 and FIG. 4 already shows how much simpler the design in FIG. 4 is and how much more safely the safety distances as required by law can be kept between the electric lines. This especially under the circumstance that it is hardly possible to prevent electrically conductive fluid, which serves for improving the electrical contact between the electrically conductive electrode 23 and the skin in a known manner, from getting into the suction line 17 as well. For example, an easily replaceable, air-permeable thrush 28 may prevent the entry of fluid as far as to the negative pressure source 18. Of course, the plug-in connectors 25, 45 26 may also be realized by recesses 15b located on the surface of the suction cup 15 opposite to the examined body.

Figure 5:
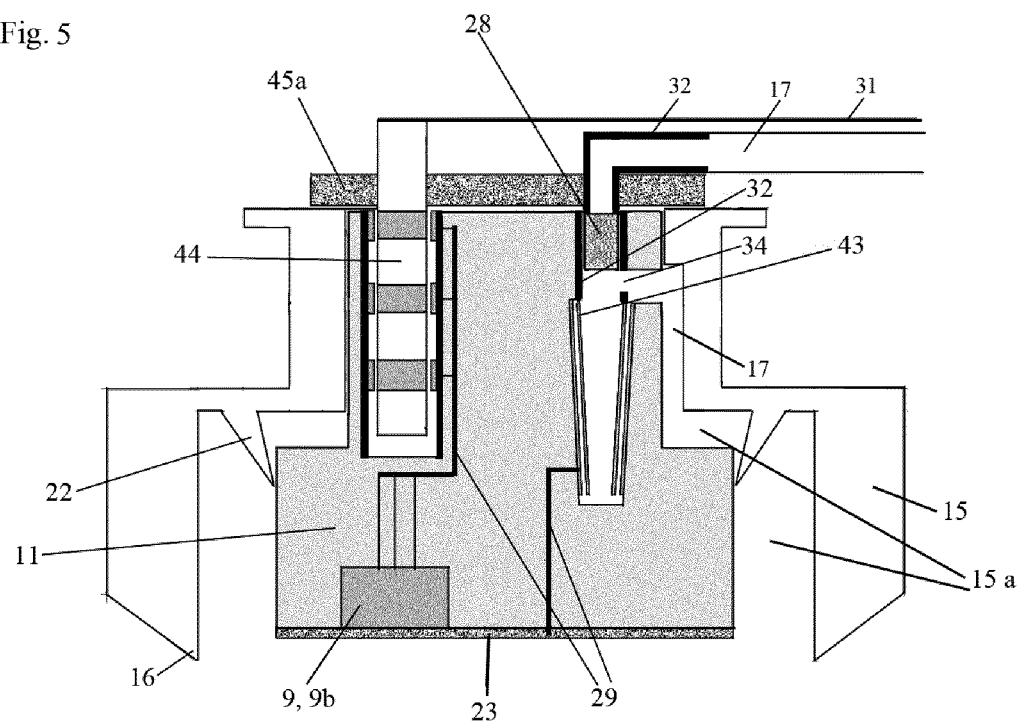
FIG. 5 shows a further embodiment of a suction electrode according to the invention.

A further embodiment as shown in FIG. 5 would consist in designing the suction cup 15 such that the electrode body 11 is able to protrude freely from the suction cup on the side facing away from the examined body, with the elastomer surrounding the electrode body 11 tightly all around the circumference of the electrode body 11, hermetically sealing it, wherein the plug-in connectors 25, 44 26 are then attached to the exposed side of the electrode body 11 facing away from the examined body. Ideally, the connector 25 and the second connector 44 are fixed jointly by a spacer 45a and designed as right angle plugs. Also in this case, the safety distances can then be kept properly. An alternative embodiment of said suction electrode, which is not shown in the figures, would consist in electrically connecting the electrode body lines 29 directly to the electrically conductive electrode 23 and the mechanical sensor 9, e.g., the accelerometer 9b, and, furthermore, in rendering the electric lines 31 pluggable with the electrode body 11 or the elastic suction cup 15, respectively. This solution is particularly convenient if the suction cup is designed according to FIG. 5, since then no recesses 15b of the elastic suction cup 15 will have to be provided in the elastomer.

Figure 6:
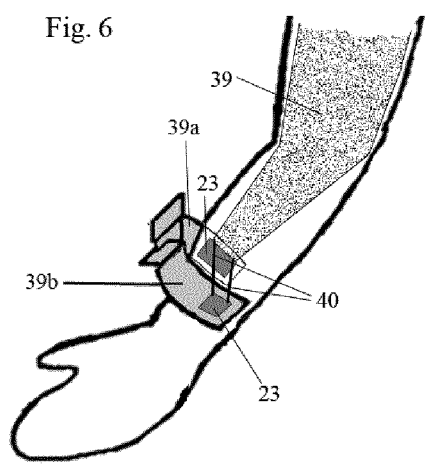
FIG. 6 shows a further embodiment of an electrode configuration according to the invention.

Various other electrode configurations have also been tested, in those studies, it has become apparent that electrodes not located on a common carrier, such as, for example, an individual terminal which supports one single electrically conductive electrode 23 each on the oppositely located separate branches, one of them being used as a feeding electrode and the other one as a measuring electrode, will also produce comparable results (FIG. 6). In this case, the electric field 39, which is drawn in a dotted way, will in fact not expand fully to the measuring electrode, however, the principle of a four-point impedance measurement is maintained and, also in this case just as in FIG. 2, the missing distance to the measuring electrode is used as an ion conductor 40, since the high ion concentration in the organism constitutes an excellent electrical conductor.

Figure 7:
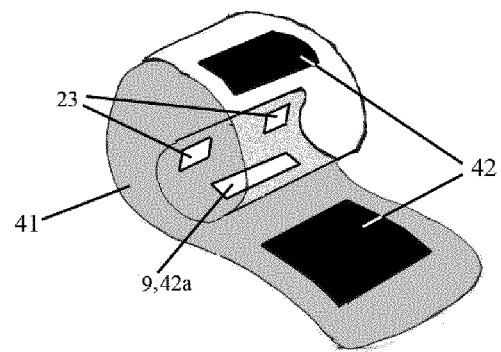
FIG. 7 shows a further embodiment of a common electrode for the recording of the ECG and for the emission and registration of additional physical parameters.

FIG. 7 shows a further embodiment of a common electrode for recording the ECG and for the emission and recording of additional physical parameters (e.g., of one or several of the parameters current, voltage, pressure, sound, light, temperature, position). According to the invention's scope of functions, 41 schematically indicates an ECG electrode which emits pressure, namely an inflatable wrist cuff 41, the Velcro® fastener is indicated with 42. With 23, the electrically conductive electrodes are indicated which are used for the ECG recording and for the impedance measurement and which, being supplied with electrode gel, are pressed properly against the wrist by the inflation of the cuff. A device for the pulse wave analysis is shown with 9. This might be, for example, a mechanical sensor 9, e.g., a pressure sensor, e.g., an accelerometer 9b, which is attached, for example, also to the wall of a liquid-filled bubble 42a. This bubble increases the area in which the mechanical sensor 9 or a different pressure sensor is able to record the pulse wave so that an accurate placing of the inflatable wrist cuff 41 is not necessary and the pulse wave can still be recorded. Along with the other signals, the pulse wave transit time, the augmentation index or the proximal and distal compliance according to Watt and Burrus (J Appl Physiol 40: 171-176, 1976) and other methods can then be recorded and analyzed, and, moreover, the arterial blood pressure can be determined at short intervals or also quasi-continuously, for example, according to the known oscillo-metric method. A non-inflatable cuff could also produce enough contact pressure of the sensors through the Velcro® fastener 42 or another fastener, only the oscillometric blood pressure measurement would then be omitted.

In countries where suction electrodes are not used due to sanitary concerns and where one-way electrodes are desired, it may prove to be useful to use adhesive electrodes instead of suction electrodes. For limb electrodes, either double electrodes on a common adhesive film 37a may be used on the neck as in FIG. 1, or else one or two individual adhesive electrodes 46 may be used.

A further version of the electrode configuration is shown in FIG. 8. This is a universal electrode which may be designed as a suction electrode or also as an adhesive electrode or also as a clamping electrode. With 11, the electrode body is indicated which includes an accelerometer 9b and a defibrillation protection 50 (depicted schematically and including all necessary components such as resistors and capacitors), wherein the electrode body lines 29 can be clamped to the electrically conductive electrode 23 by means of a push-button connection 45. Any other type of separable connection which is easy to produce (e.g., a plug connection, a clamping connection, a sliding connection, a resilient clamp etc.) could also be used instead of the push-button connection 45. The electrically conductive electrode 23 is, for example, an adhesive electrode 46 comprising a thrush 47 impregnated with an electrode gel and having an externally located adhesive surface 48 or a suction electrode with a circumferential elastic suction cup 15, as shown in FIG. 8. The electrode body can either be inserted into a suction electrode or can also be clamped to conventional adhesive electrodes 46 or also clamping electrodes 4, 5, 6, as they are provided for the limb electrodes, while the elastic suction cup 15 is, of course, omitted. The advantage is that, with only one electrode body 11 containing the defibrillation protection 50 and the mechanical sensor 99a, e.g., the accelerometer 9b, neck electrodes, chest wall electrodes as well as clamping electrodes can be operated, and, on the other hand, the electrode body 11 can be manufactured, e.g., cast, along with the board in one piece during the production of the cables. Furthermore, the electrically conductive electrode 23, which ages with use, is replaceable in case of a suction design equally easily as with disposable adhesive electrodes 46. A base plate 51 may be provided for strengthening the electrically conductive electrode. For sealing the push-button connection 45 against the surrounding humidity, a sealing, e.g., an O-ring 52, may be provided. All necessary parts such as the defibrillation protection 50, the accelerometer 9b and the push-button connection 45 can be accommodated easily on a common small board 53, the fringe of the board is drawn in a dashed way. In order that the suction line 17 can be attached automatically to the suction chamber 15a, a groove in the elastomer 54 may be provided in the elastic suction cup 15 for receiving the electric lines 31, which are depicted in a dashed way.

A transmission as inertia-free as possible of the mechanical vibrations of the thoracic wall, brought about by the 1st, 2nd or also 3rd heart sound or also via a cardiac murmur of interest, as it is observed in vitia, to the electrode is ensured and the mechanical sensor 9 can still be reused repeatedly. The electric lines 31 transmit both the electric signals and all other physical signals to the mechanical ECG impedance device 27. If, for example, only two of the 10 electrodes of the 12 channel ECG carry an accelerometer 9b, namely, e.g., one of the chest wall electrodes, e.g., V1, V2, V4, on the one hand, and a limb electrode, on the other hand, the heart sounds and the pulse wave can be recorded, resulting in an excellent analysis of the circulation times and other important circulation parameters such as, for example, also the pulse wave transit time.

Such an electrode, applied accurately, for example, above an artery located on the surface of the body, e.g., arteria radialis or arteria temporalis or arteria femoralis, arteria tibialis posterior or dorsalis pedis, is suitable for recording the pulse wave, thus performing an analysis thereof, for example, by means of a mathematical model, e.g., the windkessel model according to Watt and Burrus (J Appl Physiol 40: 171-176, 1976) or by means of the augmentation index (J Appl Physiol 40: 171-176, 1976) and, respectively, for calculating the pulse wave transit time. The concurrent recording of the volume wave by means of the impedance and of the pressure wave using the accelerometer allows additional insights into the vessel properties such as, for example, the compliance or the filling state of the vessels.

So as not to generate any falsifications as a result of using the "right leg drive" when the right leg electrode is used for impedance measurements, appropriate measures every electronics engineer is familiar with must be taken during the configuration of the current source.

For improving the reproducibility of the thorax impedance measurements, it has also proved to be useful to determine a common template from the individual templates, each obtained only by a derivation between the upper thorax aperture and an individual chest wall electrode through averaging, preferably with equal weighting of the individual templates, since, in this way, especially variations in the position of the individual chest wall electrode can also be compensated in case of examinations at different examination times for patients in long-term care, which can hardly be avoided. Therefore, it is also recommended that easily identifiable positions are determined for the peripheral electrodes, they are, for example, proximal to the wrist, ankle as well as supraclavicular.

As mentioned, for eliminating "noise" during the recording of heart sounds and cardiac murmur by the electrodes V1 to V6, the electrode positions V4r to V6r remote from the heart can be used, for example. Namely, the signal of the sensor remote from the heart could then be subtracted from the signal of the heart actions. In case a temporal shift exists between the signals, a cross-correlation of the two signals, preferably while omitting the segment carrying the heart signals, could at first also be performed and the two signals could be shifted against each other until the match is best and the correlation coefficient is largest. Only afterwards, the subtraction of the two time series, which are complete again, should be performed so that the noise of the heart signal is eliminated as far as possible and, if possible, only the useful signal remains. The electrodes remote from the heart on the thorax, especially V5r and the neck electrode, may also be used in a known manner for derivating bipolar chest wall leads, e.g., CM5, CM5-, CC5, in order to improve the sensitivity of the ergometry for detecting a coronary heart disease (Chaitman et al Circulation. 1978; 57:71-79).

In FIGS. 9 to 13, the result of measurements with the aid of the invention described herein on about 120 healthy and sick persons is shown, wherein part of the examined persons have been used in a randomized way as a calibration collective and part as an evaluation collective. For establishing the regression equations and for calibrating the present method, so-called "Gold Standard Methods" have been used, for example, BNP determination, echocardiographic parameters such as fractional shortening, EF, TAPSE, E/A and è, deuterium dilution, sodium bromide dilution, total body DXA etc. The patients are patients suffering from cardiovascular diseases, especially a chronic cardiac insufficiency, as well as patients with an impaired fluid equilibrium such as edemas, thoracic effusions, ascites.

Figure 9:
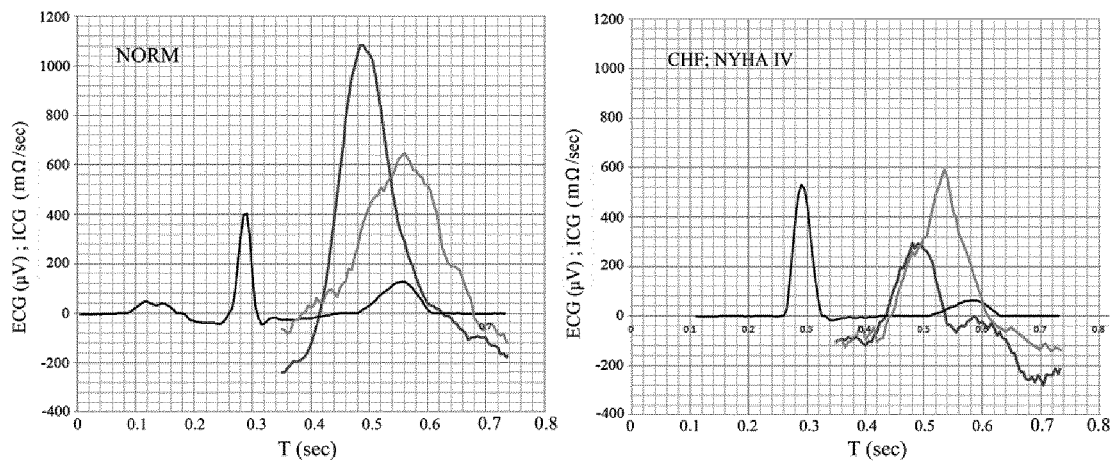

FIG. 9 exemplifies the obtained templates at the thorax and the leg in a healthy person and in a patient with heart failure. Therein, the ECG template is illustrated in black, the thorax template of the dZ/dt in dark grey and the leg template of the dZ/dt in light grey. Also the peak time, which is observed belatedly for the leg due to the volume transit time, is to be noted.

Figure 10:
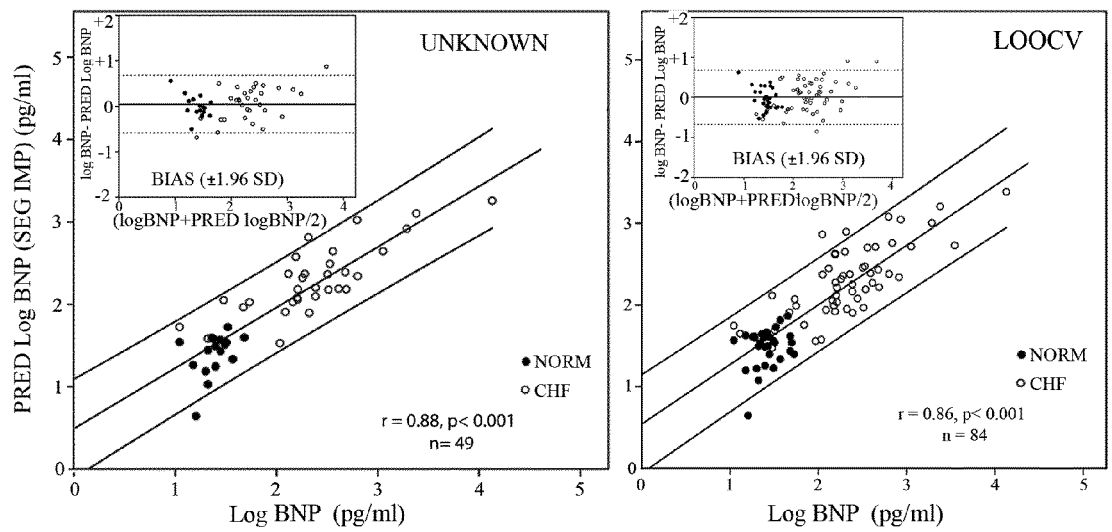

FIG. 10 shows the BNP (brain natriuretic peptide) values predicted by means of multiple regression equations. The BNP values have been logarithmized, since the distribution of the BNP corresponds to a logarithmic distribution. In this connection, the results of a multiple regression equation:

Log BNP=$f(dzt/dt$ thorax)+$f(dz/dt$ legs or arms)+$f$
($ECW/ICW$ body segment or total body, respectively)

have proved to be particularly useful, for example, wherein segments close to the heart and remote from the heart, namely the thorax segment, the abdomen segment and arm or leg segments, respectively, have been evaluated as segments.

In the left part, a prediction has been made for an unknown test collective not used for the calculation (UNKNOWN), in the right part of the figure, the LOOCV ("leave one out cross validation") method has likewise been applied to the unknown collective. As can be seen, a very good clinically usable prediction of the BNP and heart failure exists. The logarithm of the BNP can then be reconverted into the true number. The BNP is particularly interesting because it is increased both in case of a left-sided and a right-sided heart failure and both in case of a systolic and a diastolic heart failure. The insert always shows the known Bland-Altman plot. Healthy controls are indicated with NORM, patients are indicated with PTS.

Table 1 shows the prediction of a heart failure with the aid of a logistic regression with the corresponding sensitivities and specificities in comparison to a patient collective without heart failure. The original table from the SPSS program is shown. Also in this case, a remarkably good prediction of a heart failure can be made.

TABLE 1

Classification Table

| | | | prediction | | |
|---|---|---|---|---|---|
| | | | no cardiac insufficiency 0.00 | cardiac insufficiency 1.00 | percentage correct |
| | observed | | | | |
| Step 1 | no heart defect | 0.00 | 39 | 3 | 92.9 |
| | heart defect | 1.00 | 4 | 28 | 87.5 |
| | total percentage | | | | 90.5 |

The cutting data is 0.500.
Step 1: dZ/dt thorax, dZ/dt legs

Gold standard methods such as echocardiography require for those diagnoses a skilled cardiologist and an examination time of at least 20 to 30 minutes, as demanded by the German Cardiac Society and others.

Of course, instead of the BNP, all other markers which serve for estimating the cardiac output can also be used, e.g., parameters for other biochemical markers (e.g., NT-pro BNP, adrenomedullin, noradrenaline, renin, angiotensin, ADH, aldosterone, endothelin, etc., regardless of whether they have already been used or have not yet been used). Via the complex circulation analysis with an evaluation also of the peripheral vessels, it can be possible to predict also inflammation markers such as, for example, CRP, TNF-alpha, interleukin etc. or physical markers, as they are determined, for example, from the echocardiography (e.g., EF, Fractional Shortening, SV, E/A, È, PEP, LVET, Tei Index, TAPSE etc.) or from the phonocardiogram and/or from the pulse curve (e.g., PEP, LVET). In addition, other parameters which have been extracted from the ICG signal such as slopes or intervals may also be included in the equations. Also the circulation times, which have been determined, for example, from the phonocardiogram, such as, e.g., PEP and LVET, may, in addition, be included in the equations, wherein, in each case, only the highly significant predictors ($p<0.01$) are incorporated into the equation. Similarly, for example, the patient's maximum performance, e.g., in watts, VO2max, and the aerobic or, respectively, anaerobic threshold can be estimated very accurately with multiple regression equations, wherein, in this case, also the muscle mass of the various body segments, especially the legs, can be included in the regression equation in addition to the dZ or derivations thereof.

For example, those regression equations might read as follows:

VO2max(or maximum watt, or Lactate Turning Point I or II)=$f(dZ/dt$ at rest)+$f(dZ/dt$ increase during a submaximal load)+$f$(muscle mass legs)+$f$(weight)+$f$(sex, numerical)+$f$(age) etc., wherein, also in this case, only parameters which contribute significantly to the improvement of the prediction are included in the regression equation.

For diagnosing the peripheral circulatory disturbance, the change in the impedance of the limbs (arms, legs) with the heartbeat may very well be used. It is known that the shape of the rheogram (=change in the impedance of the limbs) changes particularly in the legs in case of a peripheral arterial obstructive disease (e.g., PAVK, thromboangiitis obliterans) insofar as the peak height may change, the peak time (calculated from the beginning of the steep slope) happens at another point in time, the peak becomes rounder and a loss in the dicrotic wave can be observed. All those changes can be calculated and detected, for example, by a Fourier analysis of the volume wave (see, e.g., IEEE Trans Biomed Eng 30: 387-91. 1983, Eur J Appl Physiol 89: 384-86, 2003).

It should also be noted that, of course, a reduced cardiac output and stiff vessels, which counteract a volume increase of the vessels in the limb, also change the volume wave. In this case, a mathematical correction of the volume wave for a reduced cardiac output or, respectively, for atherosclerosis may be helpful in identifying the PAVK even better. For example, a quicker volume wave transit time, as it results from the time difference at the beginning of the anacrotic phase of the impedance curve at the heart and at the limb, could also be used for identifying an atherosclerosis. In order to be able to output the pulse wave transit time in metres/seconds or another unit, it may prove to be useful to measure the distance between chest wall electrodes and symphysis or, respectively, the top of the leg (e.g., also by the transit time measurement between the electrodes) in order to then normalize the time delay between the beginning of the anacrotic wave of the dZ at the thorax and at the leg to the distance which has been covered. If an atherosclerosis and a stiffening of the vessel is provided, the peak height of the volume signal in the limb is naturally also diminished in its height. By applying additional electrodes, for example, below the knee joint (e.g., of a glue or a clamping electrode), it can also be differentiated whether the shank or the thigh is affected by the obstructive disease.

A further possibility of analyzing the volume wave is a mathematical model, e.g., a windkessel model, as described, for example, by Watt and Burrus for the peripheral pulse wave analysis.

The ratio of ECW to TBW is determined from the ratio of the base impedance (fundamental impedance) at a low frequency between, theoretically, 0 KHz (determined from the Cole-Cole plot) and, e.g., 10 kHz, e.g., 5 kHz, and a higher frequency (e.g., more than 100 kHz up to, theoretically, $\infty$ kHz, also determined via the Cole-Cole plot, e.g., 400 kHz). Discrete frequencies, e.g., in the range of 5 KHz and about 400 kHz, are likewise very sufficient for calculating the ratio ECW/TBW or ECW/ICW. It is known that the intracellular water (ICW) is determined from the difference between total body water (TBW) and extracellular water (ECW). In order to approach the true values of the in vivo ratios, the specific resistances, the resistivities, of ECW, ICW and TBW, respectively (Zhu F et al. J Appl Physiol. 2006; 100:717-24), can, in addition, be included in the equations.

Figure 11:
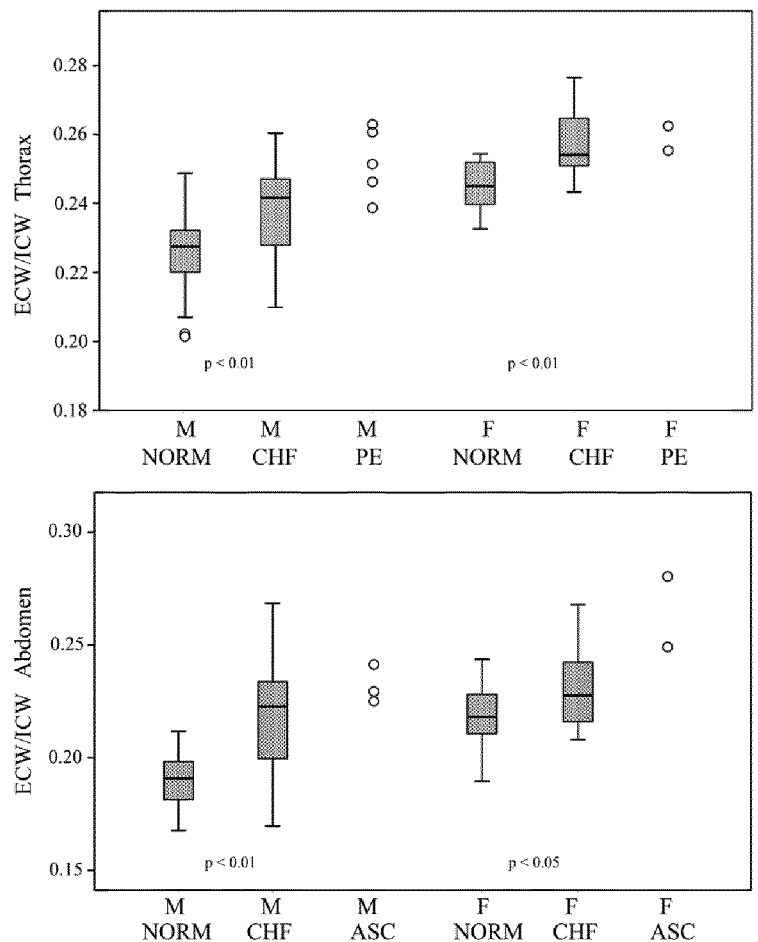

FIG. 11 also shows that said quotient is very well suited for predicting heart failure (CHF), lung water, pleural effusions (PE) as well as ascites (ASC) in men (M) and women (F), which further improves the diagnostic value of the presented application. Also the harmful visceral fat in the abdomen and one- or both-sided fluid accumulations in the legs, e.g., lymphedema, venous thromboses in the legs or leg edemas on both sides in case of heart failure or a nephrotic syndrome, can be identified well. For this purpose, regression equations determined empirically or also regression equations determined by mathematical models, taking into account anatomical dimensions, longitudinal and transverse diameters or, respectively, circumferences or, respectively, areas or, respectively, size, weight and sex (e.g., M=1, F=2), can likewise be used. Thus, the sarcopenia in the total body or in a body segment can also be estimated very well. Also in this case, only the highly significant predictors (p<0.01) are always incorporated into the equation. In both arithmetic examples, other non-linear methods such as, e.g., neural networks can, of course, also be used for the prediction.

Figure 12:
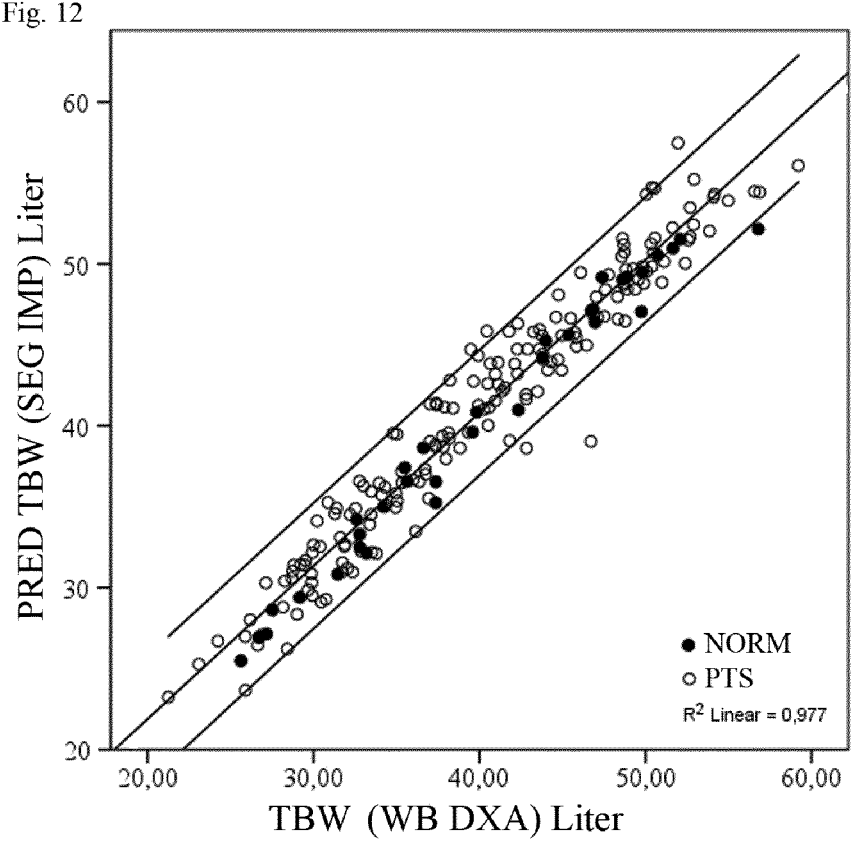

Besides calculating the ECW/TBW or ECW/ICW ratio, a remarkable prediction of the body compartments such as, e.g., the total body water (TBW), the ECW and the ICW of the "Lean Body Mass" (LBM) or the "Fat Mass" (FM) or, respectively, their variations from the standard can also be accomplished successfully with the segmental multi-frequency analysis, as exemplified in FIG. 12. A total of more than 120 healthy (NORM) and sick patients (PTS) with severe changes in the salt-water equilibrium such as, e.g., in case of heart failure, liver and kidney diseases have been used for those studies. In this connection, the regression equations read, for example, as follows:

TBW (or TBW in % of the body weight) or ECW (or ECW in % of the body weight) or TBW deviation from the desired value or ECW deviation from the desired value or muscle mass (or muscle mass in % of the body weight) or fat mass (or fat mass in % of the body weight)=$f$ (Z0 at a low frequency, e.g., 0 or 5 kHz, and/or at a high frequency, e.g., z 400 kHz or the— determined theoretically from the Cole-Cole plot–$\infty$ kHz) thorax+$f$(Z0 at 5 and/or 400 kHz) abdomen+$f$(Z0 at 5 and/or 400 kHz or $\infty$ kHz) arm+$f$(Z0 at $f$(Z0 at a low frequency, e.g., 0 or 5 kHz, and/or at a high frequency, e.g., z 400 kHz or $\infty$ kHz)) leg+$f$(Z0 at a low frequency, e.g., 0 or 5 kHz, and/or at a high frequency, e.g., z 400 kHz or $\infty$ kHz)) total body and/or sex $f$(M/=1,F=2) and/or $f$(weight) and/or $f$(size), wherein, in each case, only the highly significant predictors (p<0.01) are incorporated into the equation.

In FIG. 12, healthy controls are depicted as black circles (NORM), sick persons, "patients" (PTS), are depicted as white circles. A large part of the sick persons exhibited grave disorders in the hydration with edemas or exsiccosis. The weight of the examined persons amounted to between 37 kg in case of anorexia nervosa and 155 kg in case of severe morbid adiposity. Despite taking into account those pathological conditions, an excellent prediction can be made, as we were able to demonstrate by means of gold standard methods such as the deuterium dilution and the total body DXA (TBW-WB DXA) for determining the TBW and the sodium bromide dilution for determining the ECW. On the y-axis, the TBW predicted by means of the segmental impedance can be found (PRED TBW (SEG IMP)). Moreover, the scatter for sick persons is not significantly larger than for healthy controls. Such good results for sick persons are not known from literature, which substantiates the significance of this method for the clinical daily routine.

Figure 13:
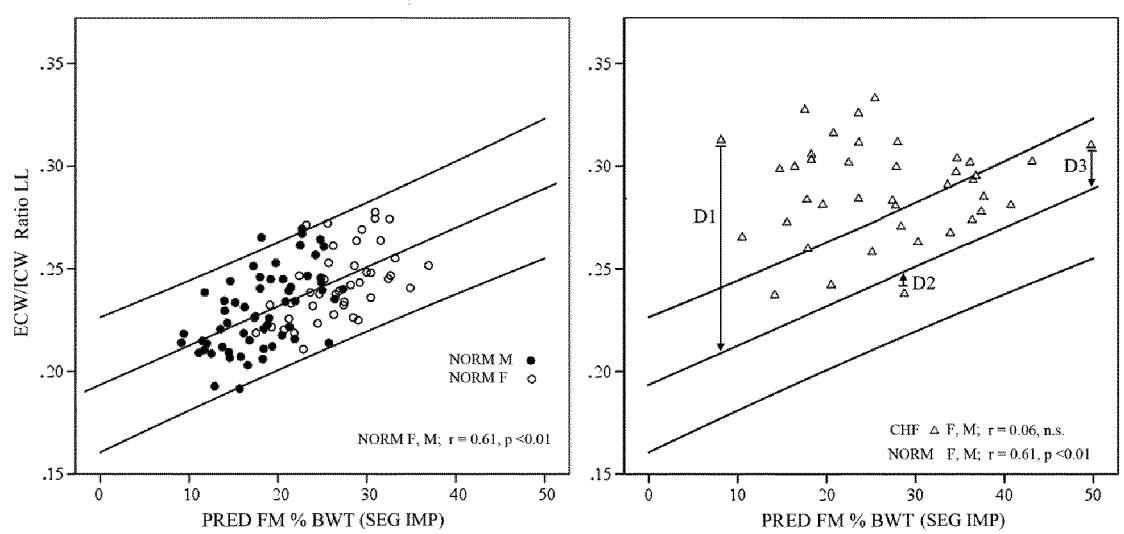

FIG. 13 shows on the x-axis the relationship between the body fat predicted from the segmental impedance="fat mass", (FM), expressed as percentage of the body weight, wherein said parameter has already been calculated exclusively with the aid of the segmental impedance measurement, as presented herein. On the y-axis, the ratio of ECW/ICW in a segment remote from the heart, for example, in the left leg, "left leg" (LL), is illustrated. On the left side in FIG. 13, healthy men (NORM M) are depicted as black circles and healthy women (NORM F) as white circles. As can be seen, healthy women have a larger ECW/ICW ratio in this illustration, apparently because they have a higher percentage of body fat. In the figure, NORM stands for normal=healthy. The significant regression line is also drawn. In the right part of the figure, male and female patients suffering from a chronic cardiac insufficiency, "chronic heart failure" (CHF), are depicted as white triangles. As can be seen and as expected, a high percentage of those patients has a substantial "fluid overload" in the extracellular space, part, however, has reached the "dry weight" in the course of the treatment. The vertical distance D to the regression line indicates the degree of over- or underhydration. D1 shows a patient with a very large overhydration, D2 and D3 indicate 2 patients with normal "dry weights". A conversion of, e.g., D1, D2, D3, into litres excess or shortage of ECW is thereby also possible.

Thus, the detection of an over- or underhydration of the organism is clearly successfully done for the first time, which previously was possible neither with an impedance analysis nor with other methods. For example, this is also of great significance for the treatment of patients with, e.g., CHF, kidney cases, chronic renal insufficiency, dialysis patients, liver diseases, pregnancy gestosis or also conditions of exsiccosis. Instead of the fat mass, of course, the opposite, namely a parameter for the "Non Fat Mass" such as the percentage of the body weight of the total body water (TBW), the lean body mass (LBM), can be used in this diagram on the x-axis, wherein the regression, of course, does not exhibit a positive, but a negative slope.

The invention claimed is:

1. An ECG (electrocardiogram) device comprising:
   ECG leads, wherein the ECG leads include ECG lead electrodes with an ECG lead function, wherein the ECG lead electrodes comprise at least limb electrodes,
   wherein at least one of the ECG lead electrodes is configured, in addition to an ECG lead function, for emitting and/or for receiving additional physical signals, including signals corresponding to at least one of electric current, voltage, pressure, sound, light, temperature, or position,
   wherein the ECG lead electrodes are configured to be arranged at a human body such that the ECG lead electrodes are spaced apart from each other and for building up an alternating current field between the ECG lead electrodes,
   wherein at least one upper thorax aperture electrode that is configured to be arranged at an upper thorax aperture, wherein the at least one upper thorax aperture electrode is selected from the ECG lead electrodes or an additional electrode and is designed for supplying an alternating current to the human body and/or for measuring an alternating current at the human body, wherein the ECG device is configured to record a change in impedance that depends on a heartbeat in at least one body segment close to the heart and in at least one body segment remote from the heart, wherein at the upper thorax aperture includes at least one of at the head, at the neck, at the back of the neck, at the shoulder, or at the arms of the human body and wherein a basic impedance at at least two frequencies is measured in at least one body segment.

2. The ECG device according to claim 1,
   wherein at least one of the ECG lead electrodes comprises an electrode body which comprises a sensor for mechanical vibrations being configured as an accelerometer, wherein a recess is provided within the electrode body, wherein the sensor for mechanical vibrations is accommodated in the recess asymmetrically opposite to an electrically conductive electrode.

3. The ECG device according to claim 2, wherein, for the evaluation of output signals provided by the sensor for mechanical vibrations, at least one frequency filter is provided, and at least one filtered frequency ranges of the output signals is analyzed, wherein the at least one frequency filter is designed as a band-pass filter with a frequency band of between 50 and 1000 Hz or as a band-pass filter with a frequency band of between 0.1 Hz and 70 Hz.

4. The ECG device according to claim 2, wherein the ECG device is configured to calculate and indicate a systolic and/or diastolic function and/or disorders thereof from a change of impedance dz/dt at the upper thorax and/or the legs determined by the electrodes and/or from physical measurement signals obtained by the at least one sensor for mechanical vibrations.

5. The ECG device according to claim 1, wherein the ECG device is configured to arithmetically estimate a physical performance, without a maximum load from measured parameters, or estimated parameters, from parameters of the accelerometer by means of regression equations and, respectively, neural networks,
   wherein the physical performance includes at least one of VO2max, a maximum wattage, a performance in percent of a standard,
   wherein the measured parameters include at least one of PEP, LVET, dZ/dtmax, and
   wherein the estimated parameters include at least muscle mass.

6. The ECG device according to claim 1, wherein the electrodes are designed for inducing an ion conduction in the body.

7. The ECG device according to claim 1, further comprising chest wall electrodes according to Wilson.

8. The ECG device according claim 1, wherein the ECG devices is configured to switch the current supply to the upper thorax aperture electrode and a distal leg electrode on one leg and to measure the impedance and a change of the impedance in dependence of the heartbeat between the electrode at the upper thorax aperture and the distal leg electrode and another distal leg electrode on the other leg.

9. The ECG device according to claim 1, wherein the ECG device is configured to switch the current supply to a distal leg electrode on one leg and to a distal leg electrode on the other leg and to measure the impedance and the change in impedance in dependence of the heartbeat between the electrode at the upper thorax aperture and alternately one of said distal leg electrodes.

10. The ECG device according to claim 1, wherein the electrode at the upper thorax aperture is designed as a double electrode on a common carrier.

11. The ECG device according to claim 1, wherein the ECG device is configured to supply an alternating electric current into the electrodes at several frequencies, the several frequencies including at least one of between 1 and 10 kHz, between 30and 200 kHz and between 200 and 1000 kHz.

12. The ECG device according to claim 11, wherein the ECG device is configured to supply the alternating electric current at an electrode of the lower limbs and at the electrode of the upper thorax aperture and wherein the measurement of the impedance occurs between the electrode of the upper thorax aperture and an electrode positionable at a lower thorax aperture, wherein the electrode of the lower thorax aperture is usable as a chest wall electrode.

13. The ECG device according to claim 1, wherein at least several of the electrodes are designed as suction electrodes, further comprising a device that controls and/or optimizes a level of a negative pressure at the suction electrodes with regard to a detected physical signal.

14. The ECG device according to claim 1, wherein the ECG device comprises a CPU that is configured to overlay several measuring curves detected by the electrodes on top of each other in order to form a template measuring curve.

15. The ECG device according to claim 1, wherein the ECG device is configured to measure the change in impedance in dependence of the heartbeat at at least two body segments and to calculate therefrom and from a measure for the extracellular volume, a cardiac output and a level of a cardiac insufficiency, and/or a biochemical parameter for a biomechanical stress of myocardium cells and/or a water accumulation and/or one of atrial natriuretic peptides, wherein the extracellular volume includes at least one of a ratio of extracellular water to total body water or a ratio of extracellular water to intracellular water and wherein the atrial natriuretic peptides include at least one of BNP, NT proBNP or adrenomedullin.

16. The ECG device according to claim 1, further comprising a CPU that is configured to calculate a relation between a parameter for a body fat and/or trunk percentage or a total body water percentage or a lean body mass, in each case based on a total body weight, and a parameter for the extracellular water that includes a ratio ECW/TBW or ECW/ICW, from the segmental impedances at low and high frequencies for segments close to the heart and/or remote from the heart or, respectively, for the total body and to output said ratio in relation to the standard values and/or a regression line.

17. The ECG device according to claim 1, further comprising a memory for storing the determined and calculated data and an interface for connecting a display and/or a printer for displaying at the display and/or printing at the printer current values and previous values of the electrical and physical parameters, which have been gathered over time, as numbers or graphically with standard panels, wherein the ECG device is designed to graphically depict, during an individual examination, the results of the measurement phases as a trend, in case that several measurement phases are provided, and, in case of a repeated examination at a later point in time, to overlay and illustrate graphically the measurement phases of the different examinations with a time identification.

18. The ECG device according to claim 1, wherein at least one of the electrodes comprises an electrode body that is provided with an easily detachable connection, which connection leads to an electrode which is designed as an adhesive electrode or a clamping electrode or an elastic band electrode, wherein the electrode body is configured to be inserted into a suction cup.

19. The ECG device according to claim 1, wherein at least one of the ECG lead electrodes is equipped with an inflatable cuff and with a sensor for mechanical vibrations that is configured as an accelerometer, wherein the sensor for mechanical vibrations is configured to be positioned at an underlying artery, the sensor for mechanical vibrations being formed in or at a liquid-filled bubble.

20. The ECG device according to claim 1, wherein at least one of the electrodes comprises joined branches, wherein one of the branches is configured as an electric current supply branch and another branch is configured as a branch for ECG and the impedance measuring.

21. The ECG device according to claim 2, wherein, for the evaluation of output signals provided by the sensor for mechanical vibrations, at least two frequency filters are provided, and at least two filtered frequency ranges of the output signals are analyzed separately, wherein at least one of the frequency filters is designed as a band-pass filter with a frequency band of between 50 and 1000 Hz and wherein at least another one of the frequency filters is designed as a band-pass filter with a frequency band of between 0.1 Hz and 70 Hz.

22. The ECG device according to claim 2, wherein the ECG device is configured to measure or arithmetically estimate a physical performance from parameters of the sensor for mechanical vibrations being configured as the accelerometer, by means of regression equations and, respectively, neural networks, wherein the parameters of the accelerometer include at least one of PEP and LVET.

23. The ECG device according claim 1, wherein the ECG device is configured to switch the current supply to distal leg electrodes on both legs and to measure the impedance and a change of the impedance in dependence of the heartbeat between the electrode at the upper thorax aperture and one of the distal leg electrodes.

24. The ECG device according claim 1, wherein the basic impedances at at least two frequencies in at least one, preferably several, body segments and the change of impedance with heart beat in at least one body segment close to the heart and in at least one body segment remote from the heart are used to diagnose heart failure class.

25. The ECG device according to claim 1, wherein pulse transit times and/or pulse wave velocity are measured from the time differences of the plethysmographic signals at different body segments.

* * * * *